US010501487B2

(12) United States Patent
Andrews et al.

(10) Patent No.: US 10,501,487 B2
(45) Date of Patent: Dec. 10, 2019

(54) ANTIBACTERIAL BISMUTH COMPLEXES

(71) Applicant: Monash University, Clayton (AU)

(72) Inventors: Philip Andrews, Upwey (AU); Melissa Werrett, Prahran (AU); Madleen Busse, Eching (DE)

(73) Assignee: MONASH UNIVERSITY, Clayton, Victoria (AU)

(*) Notice: Subject to any disclaimer, the term of this patent is extended or adjusted under 35 U.S.C. 154(b) by 0 days.

(21) Appl. No.: 15/576,531

(22) PCT Filed: May 26, 2016

(86) PCT No.: PCT/AU2016/050406
§ 371 (c)(1),
(2) Date: Nov. 22, 2017

(87) PCT Pub. No.: WO2016/187666
PCT Pub. Date: Dec. 1, 2016

(65) Prior Publication Data
US 2018/0155378 A1 Jun. 7, 2018

(30) Foreign Application Priority Data

May 26, 2015 (AU) .................................. 201501936

(51) Int. Cl.
| | | |
|---|---|---|
| *C07F 9/94* | (2006.01) | |
| *A61K 31/662* | (2006.01) | |
| *A61K 33/245* | (2019.01) | |
| *A61K 33/42* | (2006.01) | |
| *A01N 57/22* | (2006.01) | |
| *A61K 6/00* | (2006.01) | |
| *A61K 31/663* | (2006.01) | |
| *A61L 15/20* | (2006.01) | |
| *A61L 15/44* | (2006.01) | |
| *A61L 17/00* | (2006.01) | |
| *A61L 24/00* | (2006.01) | |
| *A61L 31/08* | (2006.01) | |
| *A61L 31/16* | (2006.01) | |
| *C09D 5/14* | (2006.01) | |

(52) U.S. Cl.
CPC ............... *C07F 9/94* (2013.01); *A01N 57/22* (2013.01); *A61K 6/0067* (2013.01); *A61K 31/662* (2013.01); *A61K 31/663* (2013.01); *A61K 33/245* (2013.01); *A61K 33/42* (2013.01); *A61L 15/20* (2013.01); *A61L 15/44* (2013.01); *A61L 17/005* (2013.01); *A61L 24/0015* (2013.01); *A61L 31/08* (2013.01); *A61L 31/16* (2013.01); *C09D 5/14* (2013.01); *A61L 2300/404* (2013.01); *A61L 2430/02* (2013.01)

(58) Field of Classification Search
None
See application file for complete search history.

(56) References Cited

U.S. PATENT DOCUMENTS

| | | |
|---|---|---|
| 4,049,612 A | 9/1977 | Sandler |
| 8,759,429 B2 | 6/2014 | Ni et al. |
| 2013/0146330 A1 | 6/2013 | Ni et al. |

FOREIGN PATENT DOCUMENTS

| | | |
|---|---|---|
| DE | 19510229 A1 | 9/1996 |
| DE | 19544414 A1 | 6/1997 |
| EP | 1 883 081 A1 | 1/2008 |
| KR | 10-2010-0038701 A | 4/2010 |
| WO | 2009/047353 A1 | 4/2009 |
| WO | 2010/009026 A2 | 1/2010 |
| WO | 2010/094560 A1 | 8/2010 |
| WO | 2010/106528 A1 | 9/2010 |
| WO | 2014/011515 A1 | 1/2014 |

OTHER PUBLICATIONS

Phosphinate structure: https://en.wikipedia.org/wiki/Phosphinate, 2019, pp. 1-2.*
Andrews et al. (2012) "Bismuth(III) Thiobenzoates and their Activity against Helicobacter pylori," Aust. J. Chem. 65:883-891.
Andrews et al. (Sep. 10, 2013) "Anti-Leishmanial Activity of Novel Homo- and Heteroleptic Bismuth(III) Thiocarboxylates," Aust. J. Chem. 66:1297-1305.
Chandrasekhar et al. (Apr. 12, 2013) "Lipophilic bismuth phosphates: a molecular tetradecanuclear cage and a 1D-coordination polymer. Synthesis, structure and conversion to BiPO4," Dalton Trans. 42:8709-8716.
Hardy et al. (2007) "Rapid recontamination with MRSA of the environment of an intensive care unit after decontamination with hydrogen peroxide vapour," J. Hosp. Infect. 66:360-368.
Joensson et al. (2006) "Bismuth(III) complexes with diorganodichalcogeno-phosphinato ligands. Synthesis and spectroscopic characterization," Studia Universitatis Babes-Bolyai, Chemia. 1:83-90.
Luqman et al. (Oct. 27, 2014) "Homo- and Heteroleptic Bismuth(III/V) Thiolates from N-Heterocyclic Thiones: Synthesis, Structure and Anti-Microbial Activity," Chem. A Eur. J. 20:14362-14377.
Metcalf et al. (2009) "Biosynthesis of phosphonic and phosphinic acid natural products," Annu. Rev. Biochem. 78:65-94.
Metre et al. (Oct. 19, 2015) "Bismuth Phosphinates: Temperature-Dependent Formation of a Macrocycle and 1D Coordination Polymer," Phosporus, Sulfur and Silicon. 190:2134-2141.
Payne (2008) "Desperately Seeking New Antibiotics," Science. 321:1644-1645.
Rampioni et al. (Apr. 21, 2014) "The art of antibacterial warfare: Deception through interference with quorum sensing-mediated communication," Bioorg. Chem. 55:60-68.

(Continued)

*Primary Examiner* — Clinton A Brooks
(74) *Attorney, Agent, or Firm* — Lathrop Gage LLP; Brian C. Trinque; Benjamin A. Vaughan

(57) ABSTRACT

Provided herein are organobismuth (III) phosphinate complexes, which comprise a phosphinate group and an aromatic carbocyclyl or aromatic heterocyclyl group. The complexes find use as antibacterial agents, and accordingly also provided herein are products, devices, compositions and materials comprising the complexes, for example medical products such as wound dressings and bandages.

21 Claims, 3 Drawing Sheets

(56) References Cited

OTHER PUBLICATIONS

Salvador et al. (2012) "Bismuth compounds in medicinal chemistry," Future Med. Chem. 4(11):1495-1523.
Svoboda et al. (2010) "NCN Chelated Organoantimony(III) and Organobismuth(III) Phosphinates and Phosphites: Synthesis, Structure and Reactivity," European Journal of Inorganic Chemistry. 33:5222-5230.
Yang et al. (2011) "Bismuth: Environmental Pollution and Health Effects," In; Encyclopedia of Environmental Health. Ed: Nriagu. Elsevier. Burlington, UK pp. 414-420.
International Search Report with Written Opinion corresponding to International Patent Application No. PCT/AU2016/050406, dated Aug. 1, 2016.

* cited by examiner

ANTIBACTERIAL BISMUTH COMPLEXES

CROSS-REFERENCE TO RELATED APPLICATIONS

This application is a 35 U.S.C. § 371 filing of International Application No. PCT/AU2016/050406, filed on May 26, 2016, which claims priority from Australian Provisional Patent Application No. 2015901936, filed on May 26, 2015. The entire contents of these applications are incorporated herein by reference in their entireties.

FIELD

This disclosure relates to organobismuth (III) phosphinate complexes which have antibacterial properties. This disclosure also relates to products and compositions comprising the organobismuth (III) phosphinate complexes.

BACKGROUND

The impact of the growth of multi-resistant strains of bacteria on human health. Antibacterial resistance has been identified by the World Health Organisation as one of the greatest threats we face globally, now and into the future (World Health Organization. Antimicrobial Resistance: Global report on surveillance 2014). The WHO has identified this major challenge as being one requiring urgent scientific, administrative and governmental action. Since the introduction of antibiotics 80 years ago the quantum of effective drugs has diminished dramatically. Unfortunately this coincided with a diminution of industry-based research and development into new antibiotics (T. Gottlieb, G. R. Nimmo, *Med. J. Aust.*, 2011, 194, 281). US-FDA approval of new antibacterial drugs is at an historic low, and significantly, resistance to new antibiotics can emerge rapidly. In the US, the annual costs associated with treating infectious disease is $120 billion.

In the community, and hence in hospitals, increasing numbers of bacteria; for example, MRSA (methicillin-resistant *Staphylococcus aureus*), VRE (vancomycin-resistant *Enterococcus*), multi-resistant *S. pneumonia* and *E. coli*, are now resistant to last-line antibiotics such as carbapenems, fluoroquinolines, glycopeptides and third-generation cephalosporins. There is a clear risk of bacterial infections occurring from growth of bacterial colonies and biofilms on surfaces and on medical equipment, such as medical instruments, devices, implants and the like. Antibacterial agents are known. For example, silver nanoparticles have been utilised in a range of applications including healthcare products, home consumer products, clothing and fabrics, food, construction and general disinfectants.

There is a clear need for developing novel agents having antibacterial properties. It would also be desirable to develop antibacterial agents which have properties such that they are suitable for use in preventing spread bacteria on products and surfaces, for example in hospital environments.

SUMMARY

The present inventors have identified a series of organobismuth (III) phosphinate complexes which, unlike related compounds, have strong antibacterial properties. In particular, the complexes are active against both gram-positive and gram-negative bacteria, and can be considered as having good general antibacterial properties. Accordingly, the organobismuth (III) phosphinate complexes are suitable for use in coating surfaces and for dispersing within products where antibacterial properties are desirable. The organobismuth (III) phosphinate complexes have also been found to have good thermal stability and good hydrolytic stability, properties which make them particularly suitable for use in such applications, since leaching and degradation of the complexes over time is minimised.

Accordingly, in a first aspect there is provided an organobismuth (III) phosphinate complex having a structure comprising formula (a):

(a)

wherein
$R^1$ is a phosphinate group;
$R^2$ is an aromatic carbocyclyl or aromatic heterocyclyl group; and
$R^3$ is a phosphinate group, an aromatic carbocyclyl or aromatic heterocyclyl group, or a ligand. In some embodiments $R^3$ is a phosphinate group, or an aromatic carbocyclyl or aromatic heterocyclyl group. In some embodiments $R^3$ is a phosphinate group. In some embodiments the or each phosphinate group has the formula (b)

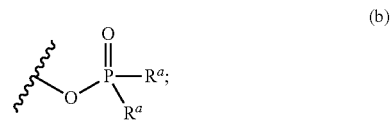

(b)

and each $R^a$ is independently selected from the group consisting of hydrogen, optionally substituted $C_{1-10}$alkyl, optionally substituted $C_{2-10}$alkenyl, optionally substituted $C_{2-10}$alkynyl, optionally substituted $C_{3-10}$ carbocyclyl and optionally substituted $C_{3-10}$ heterocyclyl. In some embodiments, the complex has the formula (c)

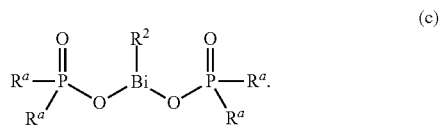

(c)

In some embodiments, the complex has the formula (d)

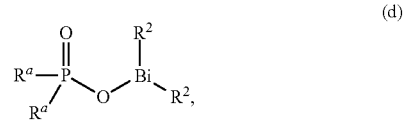

(d)

wherein each $R^2$ is independently an carbocyclyl or aromatic heterocyclyl group. In some embodiments each $R^a$ is hydrogen. In some embodiments each $R^a$ is unsubstituted $C_{1-6}$alkyl. In some embodiments each $R^a$ is $C_{6-10}$ aromatic carbocyclyl or $C_{5-10}$ aromatic heterocyclyl, said aromatic carbocyclyl or aromatic heterocyclyl being unsubstituted or substituted with up to 3 substituents selected from the group consisting of halogen, —CN, —NO$_2$, —C$_{1-6}$alkyl, —$C_{2-6}$alkenyl, —$C_{2-6}$alkynyl and —$OC_{1-6}$alkyl. In some embodiments $R^2$ is $C_{6-10}$ aromatic carbocyclyl or $C_{5-10}$ aromatic heterocyclyl, said aromatic carbocyclyl or aromatic heterocyclyl being unsubstituted or substituted with up to 3 substituents each independently selected from the group consisting of halogen, —CN, —$NO_2$, $C_{1-6}$alkyl, —$C_{2-6}$alkenyl, —$C_{2-6}$alkynyl and —$OC_{1-6}$alkyl. In some embodiments $R^2$ is phenyl which is unsubstituted or substituted with up to 3 substituents each independently selected from the group consisting of halogen, —CN, —$NO_2$, $C_{1-6}$alkyl, —$C_{2-6}$alkenyl, —$C_{2-6}$alkynyl and —$OC_{1-6}$alkyl. In some embodiments $R^a$ is selected from the group consisting of hydrogen, $C_{1-6}$alkyl, $C_{6-10}$ aromatic carbocyclyl or $C_{5-10}$ aromatic heterocyclyl, said aromatic carbocyclyl or aromatic heterocyclyl being unsubstituted or substituted with up to 3 substituents selected from the group consisting of halogen, —CN, —$NO_2$, —$C_{1-6}$alkyl, —$C_{2-6}$alkenyl, —$C_{2-6}$alkynyl and —$OC_{1-6}$alkyl; and $R^2$ is $C_{6-10}$ aromatic carbocyclyl or $C_{5-10}$ aromatic heterocyclyl, said aromatic carbocyclyl or aromatic heterocyclyl being unsubstituted or substituted with up to 3 substituents each independently selected from the group consisting of halogen, —CN, —$NO_2$, $C_{1-6}$alkyl, —$C_{2-6}$alkenyl, —$C_{2-6}$alkynyl and —$OC_{1-6}$alkyl. In some embodiments the organobismuth (III) phosphinate complex is one of example complexes 1-5a.

In a second aspect there is provided a product, device, material or composition comprising a complex as defined above. In some embodiments the product, device, material or composition is a medical product, device, material or composition. In some embodiments the product, device, material or composition for use in building construction, renovation and/or maintenance. In some embodiments the complex is distributed within the product, device, material or composition. In some embodiments the product, device, material or composition comprises an antibacterial surface coating comprising the complex. In some embodiments the composition is a polymerisable and/or curable composition. In some embodiments the product, device, material or composition is a wound dressing, a suture, a surgical implement, or a medical implant. In some embodiments the product, device, composition or material is a medical adhesive, a bone cement, a dental adhesive or a dental filler composition. In some embodiments, the product, device, material or composition is a coating, sealant, cement, concrete, grout, mortar or stucco composition. In some embodiments the product, device, material or composition is or comprises antibacterial packaging comprising the complex. In some embodiments the product, device, material or composition is a cellulosic material.

DETAILED DESCRIPTION

Specific Terms

Figure 1:
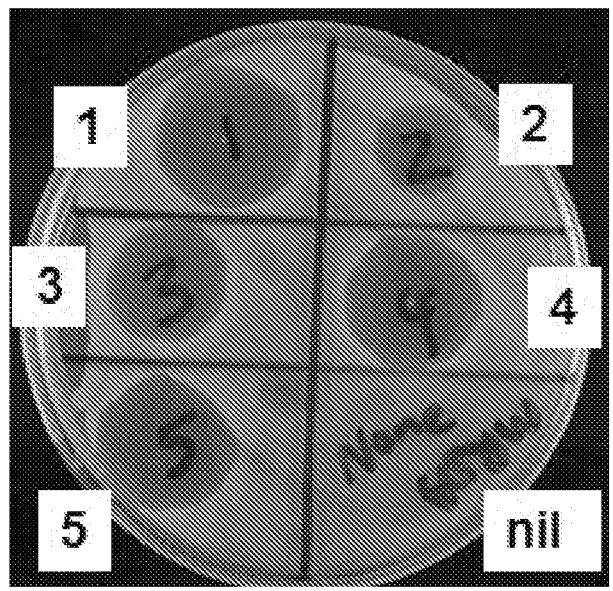
FIG. 1 shows a photograph of a zone of inhibition test showing inhibition of growth of MRSA on BHI agar by example complexes 1-5.

As used herein, the term "alkyl" encompasses straight and branched chain saturated hydrocarbon groups. Examples of alkyl groups include methyl, ethyl, n-propyl, iso-propyl, n-butyl, t-butyl, i-butyl, sec-butyl, pentyl and hexyl groups.

As used herein, the term "alkoxy" means the group O-alkyl, where "alkyl" is used as described above. Examples of alkoxy groups include methoxy and ethoxy groups. Other examples include propoxy and butoxy.

As used herein, the term "alkenyl" encompasses both straight and branched chain unsaturated hydrocarbon groups with at least one carbon-carbon double bond. Examples of alkenyl groups include ethenyl, propenyl, butenyl, pentenyl and hexenyl. Preferred alkenyl groups include ethenyl, 1-propenyl, 2-propenyl and but-2-enyl.

As used herein, the term "alkynyl" encompasses both straight and branched chain unsaturated hydrocarbon groups with at least one carbon-carbon triple bond. Examples of alkynyl groups include ethynyl, propynyl, butynyl, pentynyl and hexynyl. Preferred alkynyl groups include ethynyl, 1-propynyl and 2-propynyl.

As used herein, the terms "halo" or "halogen", whether employed alone or in compound words such as haloalkyl, means fluorine, chlorine, bromine or iodine.

As used herein, the term "haloalkyl" means an alkyl group having at least one halogen substituent, the terms "alkyl" and "halogen" being understood to have the meanings outlined above. Similarly, the term "monohaloalkyl" means an alkyl group having a single halogen substituent, the term "dihaloalkyl" means an alkyl group having two halogen substituents and the term "trihaloalkyl" means an alkyl group having three halogen substituents. Examples of monohaloalkyl groups include fluoromethyl, chloromethyl, bromomethyl, fluoromethyl, fluoropropyl and fluorobutyl groups; examples of dihaloalkyl groups include difluoromethyl and difluoroethyl groups; examples of trihaloalkyl groups include trifluoromethyl and trifluoroethyl groups.

As used herein, the terms "carbocyclic" and "carbocyclyl" represent a ring system wherein the ring atoms are all carbon atoms, e.g., from 3 to 20 carbon ring atoms, and which may be aromatic, non-aromatic, saturated, or unsaturated. The terms encompass single ring systems, e.g. cycloalkyl groups such as cyclopentyl and cyclohexyl, aromatic groups such as phenyl, and cycloalkenyl groups such as cyclohexenyl, as well as fused-ring systems such as naphthyl and fluorenyl.

As used herein, the terms "heterocyclic' and "heterocyclyl" represent an aromatic or a non-aromatic cyclic group of carbon atoms wherein from one to three of the carbon atoms is/are replaced by one or more heteroatoms independently selected from nitrogen, oxygen or sulfur. A heterocyclyl group may, for example, be monocyclic or polycyclic, and contain for example from 3 to 20 ring atoms. In a bicyclic heterocyclyl group there may be one or more heteroatoms in each ring, or only in one of the rings.

Examples of heterocyclyl groups include piperidinyl, tetrahydrofuranyl, tetrahydropyranyl, pyridyl, pyrimidinyl and indolyl.

As used herein, the term "cycloalkyl" represents a ring system wherein the ring atoms are all carbon atoms, e.g., from 3 to 20 carbon ring atoms, and which is saturated. A cycloalkyl group can be monocyclic or polycyclic. A bicyclic group may, for example, be fused or bridged. Examples of monocyclic cycloalkyl groups include cyclopropyl, cyclobutyl and cyclopentyl. Other examples of monocyclic cycloalkyl groups are cyclohexyl, cycloheptyl and cyclooctyl. Examples of bicyclic cycloalkyl groups include bicyclo [2.2.1]hept-2-yl.

As will be understood, an "aromatic" group means a cyclic group having 4m+2 π electrons, where m is an integer equal to or greater than 1. As used herein, "aromatic" is used interchangeably with "aryl" to refer to an aromatic group, regardless of the valency of aromatic group.

As used herein, the terms "aromatic carbocyclyl" or "aromatic carbocycle" represent a ring system which is aromatic and in which the ring atoms are all carbon atoms, e.g. having from 6-14 ring atoms. An aromatic carbocyclyl group may be monocyclic or polycyclic. Examples of aromatic carbocyclyl groups include phenyl, naphthyl and fluorenyl. Polycyclic aromatic carbocyclyl groups include those in which only one of the rings is aromatic, such as for example indanyl.

As used herein, the terms "aromatic heterocycle" or "aromatic heterocyclyl" represent an aromatic cyclic group of carbon atoms wherein from one to three of the carbon atoms is/are replaced by one or more heteroatoms independently selected from nitrogen, oxygen or sulphur, e.g. having from 5-14 ring atoms. The term "aromatic heterocyclyl" is used interchangeably with 'heteroaryl". An aromatic heterocyclyl group may be monocyclic or polycyclic. Examples of monocyclic aromatic heterocyclyl groups (also referred to as monocyclic heteroaryl groups) include furanyl, thienyl, pyrrolyl, imidazolyl, pyridyl and pyrimidinyl. Examples of polycyclic aromatic heterocyclyl groups (also referred to as bicyclic heteroaryl groups) include benzimidazolyl, quinolinyl and indolyl. Polycyclic aromatic heterocyclyl groups include those in which only one of the rings is an aromatic heterocycle.

As used herein, the term "cyano" represents a —CN moiety.

As used herein, the term "hydroxyl" represents a —OH moiety.

As used herein, the term "alkoxy" represents an —O-alkyl group in which the alkyl group is as defined supra. Examples include methoxy, ethoxy, n-propoxy, iso-propoxy, and the different butoxy, pentoxy, hexyloxy and higher isomers.

As used herein, the term "aryloxy" represents an —O-aryl group in which the aryl group is as defined supra. Examples include, without limitation, phenoxy and naphthoxy.

As used herein, the term "carboxyl" represents a —$CO_2$ moiety.

As used herein, the term "nitro" represents a —$NO_2$ moiety.

The term "optionally fused" means that a group is either fused to another ring system or unfused, and "fused" refers to one or more rings that share at least two common ring atoms with one or more other rings. Fusing may be provided by one or more carbocyclic or heterocyclic rings, as defined herein, or be provided by substituents of rings being joined together to form a further ring system. The fused ring may be a 5, 6 or 7-membered ring of between 5 and 10 ring atoms in size. The fused ring may be fused to one or more other rings, and may for example contain 1 to 4 rings.

The term "optionally substituted" means that a functional group is either substituted or unsubstituted, at any available position.

General Terms

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or groups of compositions of matter. Thus, as used herein, the singular forms "a", "an" and "the" include plural aspects unless the context clearly dictates otherwise. For example, reference to "a" includes a single as well as two or more; reference to "an" includes a single as well as two or more; reference to "the" includes a single as well as two or more and so forth.

Those skilled in the art will appreciate that the disclosure herein is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

Each example of the present disclosure described herein is to be applied mutatis mutandis to each and every other example unless specifically stated otherwise. The present disclosure is not to be limited in scope by the specific examples described herein, which are intended for the purpose of exemplification only. Functionally-equivalent products, compositions and methods are clearly within the scope of the disclosure as described herein.

The term "and/or", e.g., "X and/or Y" shall be understood to mean either "X and Y" or "X or Y" and shall be taken to provide explicit support for both meanings or for either meaning.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

It will be clearly understood that, although a number of prior art publications are referred to herein, this reference does not constitute an admission that any of these documents forms part of the common general knowledge in the art, in Australia or in any other country.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

Organobismuth (III) Phosphinate Complexes

As used herein, the term "organobismuth" refers to a moiety comprising a carbon to bismuth bond. In the organobismuth complexes of the present disclosure, bismuth is present in an oxidation state of +3, also referred to as bismuth (III) or Bi (III). The organobismuth (III) phosphinate complexes of the present disclosure have a structure comprising formula (a):

(a)

It will be appreciated that the bismuth may comprise isotopes.

The coordination number of a metal complex refers to the number of ligands (i.e. donor atoms) attached to the metal. For example, in the organobismuth (III) phosphinate complexes of the present disclosure, the bismuth has a coordination number of at least three, for example it may be coordinated by or bonded to at least three groups such as two phosphinate groups and one aromatic carbocyclyl group. In some embodiments the bismuth may have a higher coordination number, for example it may additionally be coordinated by a neutral molecule such as $H_2O$. However, in other embodiments the bismuth has a coordination number of three, i.e. the organobismuth (III) phosphinate complex has a structure consisting of formula (a).

In the structure of formula (a) $R^1$ is a phosphinate group. The bismuth is bonded to the phosphinate group through a Bi—O—P linkage. The phosphinate group may for example have the formula (b)

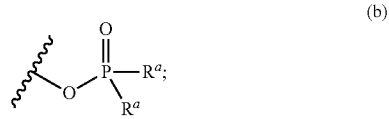
(b)

wherein each $R^a$ is independently selected from the group consisting of hydrogen, optionally substituted $C_{1-10}$alkyl, optionally substituted $C_{2-10}$alkenyl, optionally substituted $C_{2-10}$alkynyl, optionally substituted $C_{3-10}$ carbocyclyl and optionally substituted $C_{3-10}$ heterocyclyl. Where $R^a$ is substituted $C_{1-10}$alkyl, substituted $C_{2-10}$alkenyl, substituted $C_{2-10}$alkynyl, substituted $C_{3-10}$ carbocyclyl or optionally substituted $C_{3-10}$ heterocyclyl, the alkyl, alkenyl, alkynyl, carbocyclyl or heterocyclyl group may for example contain 1, 2 or 3 substituents. In some embodiments, each $R^a$ is independently selected from the group consisting of hydrogen, $C_{1-10}$alkyl, $C_{2-10}$alkenyl, $C_{2-10}$alkynyl, $C_{3-10}$ carbocyclyl and $C_{3-10}$ heterocyclyl, said alkyl, alkenyl, alkynyl, cycloalkyl, carbocyclyl or heterocyclyl being unsubstituted or substituted with up to 3 substituents each independently selected from the group consisting of halogen, —CN, —NO₂, —C(O)N($R^b$)₂, —C(O)$R^b$, —S(O)₂N($R^b$)₂, —C(O)O$R^b$; —$R^b$, —O$R^b$, —OC(O)$R^b$, —N($R^b$)₂, —N($R^b$)C(O)$R^b$ and —N($R^b$)S(O)₂$R^b$: and wherein each $R^b$ is independently selected from the group consisting of hydrogen, $C_{1-6}$alkyl, $C_{1-6}$alkenyl, $C_{1-6}$alkynyl, $C_{3-10}$cycloalkyl, $C_{6-10}$ aromatic carbocyclyl and $C_{5-10}$ aromatic heterocyclyl, said alkyl, alkenyl, alkynyl, cycloalkyl, aromatic carbocyclyl or aromatic heterocyclyl being unsubstituted or substituted with up to 3 substituents each independently selected from the group consisting of halogen, —CN, hydroxyl, —$C_{1-6}$alkyl, —$C_{2-6}$alkenyl, —$C_{2-6}$alkynyl, —O$C_{1-6}$alkyl, —$C_{1-6}$haloalkyl, —NH₂, —NH$C_{1-6}$alkyl and —N($C_{1-6}$alkyl)₂.

In some embodiments at least one $R^a$ is hydrogen. In some embodiments each $R^a$ is hydrogen.

In some embodiments each $R^a$ is $C_{1-10}$alkyl which is unsubstituted or substituted with up to 3 substituents each independently selected from the group consisting of halogen, —CN, hydroxyl, —O$C_{1-6}$alkyl, NH₂, —NH$C_{1-6}$alkyl, —N($C_{1-6}$alkyl)₂ and $C_{6-10}$ aromatic carbocyclyl, which aromatic carbocyclyl is unsubstituted or substituted with up to 3 substituents each independently selected from halogen, —CN, hydroxyl, —$C_{1-6}$alkyl, —O$C_{1-6}$alkyl and —$C_{1-6}$haloalkyl. In some embodiments each $R^a$ is $C_{1-6}$alkyl which is unsubstituted or substituted with up to 3 substituents each independently selected from the group consisting of halogen, hydroxyl, phenyl, —O$C_{1-4}$alkyl, NH₂, —NH$C_{1-4}$alkyl and —N($C_{1-4}$alkyl)₂. In some embodiments each $R^a$ is $C_{1-6}$alkyl. In some embodiments each $R^a$ is methyl, ethyl, n-propyl or i-propyl.

In some embodiments each $R^a$ is independently $C_{6-10}$aromatic carbocyclyl or $C_{5-10}$ aromatic heterocyclyl, said aromatic carbocyclyl or aromatic heterocyclyl being unsubstituted or substituted with up to 3 substituents each independently selected from the group consisting of halogen, —CN, —NO₂, —C(O)N($R^b$)₂, —C(O)$R^b$, —S(O)₂N($R^b$)₂, —C(O)O$R^b$; —$R^b$, —O$R^b$, —OC(O)$R^b$, —N($R^b$)₂, —N($R^b$)C(O)$R^b$ and —N($R^b$)S(O)₂$R^b$; and wherein each $R^b$ is independently selected from the group consisting of hydrogen, $C_{1-6}$alkyl, $C_{1-6}$alkenyl, $C_{1-6}$alkynyl, $C_{3-10}$cycloalkyl, $C_{6-10}$ aromatic carbocyclyl and $C_{5-10}$ aromatic heterocyclyl, said alkyl, alkenyl, alkynyl, cycloalkyl, aromatic carbocyclyl or aromatic heterocyclyl being unsubstituted or substituted with up to 3 substituents each independently selected from the group consisting of halogen, —CN, hydroxyl, —$C_{1-6}$alkyl, —$C_{2-6}$alkenyl, —$C_{2-6}$alkynyl, —O$C_{1-6}$alkyl, —$C_{1-6}$haloalkyl, —NH₂, —NH$C_{1-6}$alkyl and —N($C_{1-6}$alkyl)₂. In some embodiments each $R^a$ is independently $C_{6-10}$ aromatic carbocyclyl or $C_{5-10}$ aromatic heterocyclyl, said aromatic carbocyclyl or aromatic heterocyclyl being unsubstituted or substituted with up to 3 substituents each independently selected from the group consisting of halogen, —CN, —NO₂, hydroxyl, —$C_{1-6}$alkyl, —$C_{2-6}$alkenyl, —$C_{2-6}$alkynyl, —O$C_{1-6}$alkyl, —$C_{1-6}$haloalkyl, —NH₂, —NH$C_{1-6}$alkyl and —N($C_{1-6}$alkyl)₂. In some embodiments each $R^a$ is $C_{6-10}$ aromatic carbocyclyl or $C_{5-10}$ aromatic heterocyclyl, said aromatic carbocyclyl or aromatic heterocyclyl being unsubstituted or substituted with up to 3 substituents selected from the group consisting of halogen, —CN, —NO₂, —$C_{1-6}$alkyl, —$C_{2-6}$alkenyl, —$C_{2-6}$alkynyl and —O$C_{1-6}$alkyl. In some embodiments each $R^a$ is phenyl which is unsubstituted or substituted with up to 3 substituents each independently selected from the group consisting of halogen, —CN, —NO₂, $C_{1-6}$alkyl, —$C_{2-6}$alkenyl, —$C_{2-6}$alkynyl and —O$C_{1-6}$alkyl. In some embodiments $R^a$ is a phenyl group which comprises an ortho-substituent. In some embodiments $R^a$ is a phenyl group which comprises a meta-substituent. In some embodiments $R^a$ is a phenyl group which comprises a para-substituent. In some embodiments $R^a$ is phenyl which is unsubstituted or substituted with one —NO₂ group or one —OMe group. In some embodiments $R^a$ is

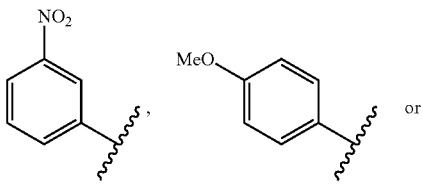
or

-continued

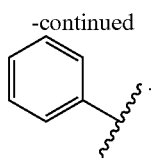

In some embodiments of the phosphinate group of formula (b), one $R^a$ is hydrogen and the other $R^a$ is phenyl.

In the structure of formula (a), $R^2$ is an aromatic carbocyclyl or aromatic heterocyclyl group bonded to bismuth through a bismuth-carbon bond. The aromatic carbocyclyl or aromatic heterocyclyl group may be unsubstituted or substituted. Where the aromatic carbocyclyl or aromatic heterocyclyl group is substituted, it is bonded to bismuth through a bond between the bismuth and a carbon atom present in the aromatic carbocyclyl or aromatic heterocyclyl ring system. Where the aromatic carbocyclyl or aromatic heterocyclyl group is substituted, it may for example contain 1, 2 or 3 substituents. In some embodiments, $R^2$ is an optionally substituted $C_{6-10}$ aromatic carbocyclyl or an optionally substituted $C_{5-10}$ aromatic heterocyclyl.

In some embodiments $R^2$ is a $C_{6-10}$ aromatic carbocyclyl or $C_{5-10}$ aromatic heterocyclyl, said aromatic carbocyclyl or aromatic heterocyclyl being unsubstituted or substituted with up to 3 substituents each independently selected from the group consisting of $C_{1-6}$alkyl, $C_{2-6}$ alkenyl, $C_{2-6}$alkynyl, —$OC_{1-6}$alkyl, halogen, —CN, —$NO_2$, —$C(O)N(R^b)_2$, —$C(O)R^b$, —$S(O)_2N(R^b)_2$, —$C(O)OR^b$; —$R^b$, —$OR^b$, —$OC(O)R^b$, —$N(R^b)_2$, —$N(R^b)C(O)R^b$ and —$N(R^b)S(O)_2R^b$; and wherein each $R^b$ is independently selected from the group consisting of hydrogen, $C_{1-6}$alkyl, $C_{1-6}$alkenyl, $C_{1-6}$alkynyl, $C_{3-10}$cycloalkyl, $C_{6-10}$ aromatic carbocyclyl and $C_{5-10}$ aromatic heterocyclyl, said alkyl, alkenyl, alkynyl, cycloalkyl, aromatic carbocyclyl or aromatic heterocyclyl being unsubstituted or substituted with up to 3 substituents each independently selected from the group consisting of halogen, —CN, hydroxyl, —$C_{1-6}$alkyl, —$C_{2-6}$alkenyl, —$C_{2-6}$alkynyl, —$OC_{1-6}$alkyl, —$C_{1-6}$haloalkyl, —$NH_2$, —$NHC_{1-6}$alkyl and —$N(C_{1-6}$alkyl$)_2$. In some embodiments $R^2$ is a $C_{6-10}$ aromatic carbocyclyl or $C_{5-10}$ aromatic heterocyclyl, said aromatic carbocyclyl or aromatic heterocyclyl being unsubstituted or substituted with up to 3 substituents each independently selected from the group consisting of halogen, —CN, —$NO_2$, —$C(O)N(R^b)_2$, —$C(O)R^b$, —$S(O)_2N(R^b)_2$, —$C(O)OR^b$; —$R^b$, —$OR^b$, —$OC(O)R^b$, —$N(R^b)_2$, —$N(R^b)C(O)R^b$ and —$N(R^b)S(O)_2R^b$; and wherein each $R^b$ is independently selected from the group consisting of hydrogen, $C_{1-6}$alkyl, $C_{1-6}$alkenyl, $C_{1-6}$alkynyl, $C_{3-10}$cycloalkyl, $C_{6-10}$ aromatic carbocyclyl and $C_{5-10}$ aromatic heterocyclyl, said alkyl, alkenyl, alkynyl, cycloalkyl, aromatic carbocyclyl or aromatic heterocyclyl being unsubstituted or substituted with up to 3 substituents each independently selected from the group consisting of halogen, —CN, hydroxyl, —$C_{1-6}$alkyl, —$C_{2-6}$alkenyl, —$C_{2-6}$alkynyl, —$OC_{1-6}$alkyl, —$C_{1-6}$haloalkyl, —$NH_2$, —$NHC_{1-6}$alkyl and —$N(C_{1-6}$alkyl$)_2$. In some embodiments $R^2$ is $C_{6-10}$ aromatic carbocyclyl or $C_{5-10}$ aromatic heterocyclyl, said aromatic carbocyclyl or aromatic heterocyclyl being unsubstituted or substituted with up to 3 substituents each independently selected from the group consisting of halogen, —CN, —$NO_2$, hydroxyl, —$C_{1-6}$alkyl, —$C_{2-6}$alkenyl, —$C_{2-6}$alkynyl, —$OC_{1-6}$alkyl, —$C_{1-6}$haloalkyl, —$NH_2$, —$NHC_{1-6}$alkyl and —$N(C_{1-6}$alkyl$)_2$. In some embodiments each $R^2$ is $C_{6-10}$ aromatic carbocyclyl or $C_{5-10}$ aromatic heterocyclyl, said aromatic carbocyclyl or aromatic heterocyclyl being unsubstituted or substituted with up to 3 substituents selected from the group consisting of halogen, —CN, —$NO_2$, —$C_{1-6}$alkyl, —$C_{2-6}$alkenyl, —$C_{2-6}$alkynyl and —$OC_{1-6}$alkyl. In some embodiments $R^2$ is phenyl which is unsubstituted or substituted with up to 3 substituents each independently selected from the group consisting of halogen, —CN, —$NO_2$, $C_{1-6}$alkyl, —$C_{2-6}$alkenyl, —$C_{2-6}$alkynyl and —$OC_{1-6}$alkyl. In some embodiments $R^2$ is phenyl which is unsubstituted or substituted with 1 or 2 substituents each independently selected from the group consisting of halogen, —CN, —$NO_2$, —$C_{1-6}$alkyl, —$C_{2-6}$alkenyl, —$C_{2-6}$alkynyl and —$OC_{1-6}$alkyl. In some embodiments $R^2$ is a phenyl group which comprises an ortho substituent. In some embodiments $R^2$ is a phenyl group which comprises a meta-substituent. In some embodiments $R^2$ is a phenyl group which comprises a para-substituent. In some embodiments $R^2$ is unsubstituted phenyl. In some embodiments $R^2$ is styrenyl

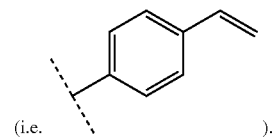

(i.e. ).

In the structure of formula (I), $R^3$ is a phosphinate group, an aromatic carbocyclyl or aromatic heterocyclyl group bonded to bismuth through a bismuth-carbon bond, or a ligand. Where $R^3$ is a phosphinate group, the definitions for the phosphinate are as defined above for $R^1$. Where $R^3$ is an aromatic carbocyclyl or aromatic heterocyclyl group bonded to bismuth through a bismuth-carbon bond, the definitions for the aromatic carbocyclyl or aromatic heterocyclyl group are as defined above for $R^2$. In some embodiments, $R^3$ is a phosphinate group having the formula (b)

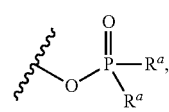

(b)

wherein each $R^a$ is independently selected from the group consisting of hydrogen, $C_{1-10}$alkyl, $C_{2-10}$alkenyl, $C_{2-10}$alkynyl, $C_{3-10}$ carbocyclyl and $C_{3-10}$ heterocyclyl, said alkyl, alkenyl, alkynyl, cycloalkyl, carbocyclyl or heterocyclyl being unsubstituted or substituted with up to 3 substituents each independently selected from the group consisting of halogen, —CN, —$NO_2$, —$C(O)N(R^b)_2$, —$C(O)R^b$, —$S(O)_2N(R^b)_2$, —$C(O)OR^b$; —$R^b$, —$OR^b$, —$OC(O)R^b$, —$N(R^b)_2$, —$N(R^b)C(O)R^b$ and —$N(R^b)S(O)_2R^b$: and wherein each $R^b$ is independently selected from the group consisting of hydrogen, $C_{1-6}$alkyl, $C_{1-6}$alkenyl, $C_{1-6}$alkynyl, $C_{3-10}$cycloalkyl, $C_{6-10}$ aromatic carbocyclyl and $C_{5-10}$ aromatic heterocyclyl, said alkyl, alkenyl, alkynyl, cycloalkyl, aromatic carbocyclyl or aromatic heterocyclyl being unsubstituted or substituted with up to 3 substituents each independently selected from the group consisting of halogen, —CN, hydroxyl, —$C_{1-6}$alkyl, —$C_{2-6}$alkenyl, —$C_{2-6}$alkynyl, —$OC_{1-6}$ alkyl, —$C_{1-6}$haloalkyl, —$NH_2$, —$NHC_{1-6}$alkyl and —$N(C_{1-6}$alkyl$)_2$. In some embodiments, $R^3$ is a phosphinate group having the formula (b)

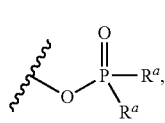

(b)

wherein each $R^a$ is independently selected from the group consisting of hydrogen, methyl,

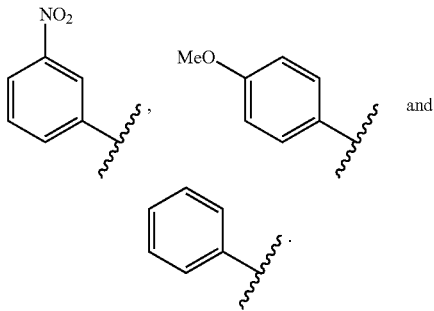

and

In some embodiments $R^3$ is a $C_{6-10}$ aromatic carbocyclyl or $C_{5-10}$ aromatic heterocyclyl, said aromatic carbocyclyl or aromatic heterocyclyl being unsubstituted or substituted with up to 3 substituents each independently selected from the group consisting of $C_{1-6}$alkyl, $C_{2-6}$ alkenyl, $C_{2-6}$alkynyl, —$OC_{1-6}$alkyl, halogen, —CN, —$NO_2$, —C(O)N($R^b$)$_2$, —C(O)$R^b$, —S(O)$_2$N($R^b$)$_2$, —C(O)O$R^b$; —$R^b$, —O$R^b$, —OC(O)$R^b$, —N($R^b$)$_2$, —N($R^b$)C(O)$R^b$ and —N($R^b$)S(O)$_2R^b$; and wherein each $R^b$ is independently selected from the group consisting of hydrogen, $C_{1-6}$alkyl, $C_{1-6}$alkenyl, $C_{1-6}$alkynyl, $C_{3-10}$cycloalkyl, $C_{6-10}$ aromatic carbocyclyl and $C_{5-10}$ aromatic heterocyclyl, said alkyl, alkenyl, alkynyl, cycloalkyl, aromatic carbocyclyl or aromatic heterocyclyl being unsubstituted or substituted with up to 3 substituents each independently selected from the group consisting of halogen, —CN, hydroxyl, —$C_{1-6}$alkyl, —$C_{2-6}$alkenyl, —$C_{2-6}$alkynyl, —$OC_{1-6}$alkyl, —$C_{1-6}$haloalkyl, —$NH_2$, —$NHC_{1-6}$alkyl and —N($C_{1-6}$alkyl)$_2$. In some embodiments, $R^3$ is phenyl. In some embodiments $R^3$ is styrenyl.

In some embodiments, $R^3$ is a ligand. The ligand may be any group (e.g. an ionic or neutral species) other than an $R^1$ or $R^2$ which is capable of bonding to bismuth, such that the resulting organobismuth (III) complex is suitable for use as an antibacterial additive in antibacterial coating compositions or for use as an antibacterial additive for dispersal within a product. In some embodiments $R^3$ is a phosphinate group, or an aromatic carbocyclyl or aromatic heterocyclyl group bonded to bismuth through a bismuth-carbon bond. In some embodiments, $R^3$ is an aromatic carbocyclyl or aromatic heterocyclyl group bonded to bismuth through a bismuth-carbon bond. In some embodiments, $R^3$ is a phosphinate group. In some embodiments, the bismuth may be bonded to two phosphinate groups which are part of the same moiety, i.e. a bidentate moiety.

In some embodiments the organobismuth (III) phosphinate complex of the present disclosure has a structure comprising formula (c):

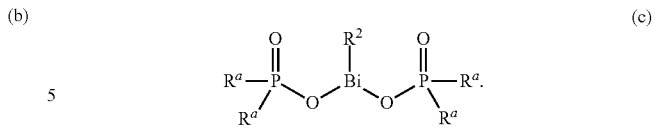

(c)

In some embodiments the organobismuth (III) phosphinate complex has a structure consisting of formula (c). The definitions for the $R^a$ and $R^2$ groups in the complex of formula (c) are as defined above with respect to formulae (a) and (b). For example, in some embodiments where the complex has the formula (c), each $R^a$ is hydrogen. In some embodiments, at least one of the $R^a$ groups attached to each phosphorous is hydrogen. In other embodiments where the complex has the formula (c), each $R^a$ is $C_{1-6}$alkyl. In other embodiments where the complex has the formula (c), each $R^a$ is $C_{6-10}$ aromatic carbocyclyl or $C_{5-10}$ aromatic heterocyclyl, said aromatic carbocyclyl or aromatic heterocyclyl being unsubstituted or substituted with up to 3 substituents selected from the group consisting of halogen, —CN, —$NO_2$, —$C_{1-6}$alkyl, —$C_{2-6}$alkenyl, —$C_{2-6}$alkynyl and —$OC_{1-6}$alkyl. In some embodiments of the compound of formula (c), one of the $R^a$ groups attached to each phosphorous is hydrogen and the other is phenyl. In some embodiments where the complex has the formula (c), $R^2$ is $C_{6-10}$ aromatic carbocyclyl or $C_{5-10}$ aromatic heterocyclyl, said aromatic carbocyclyl or aromatic heterocyclyl being unsubstituted or substituted with up to 3 substituents each independently selected from the group consisting of halogen, —CN, —$NO_2$, $C_{1-6}$alkyl, —$C_{2-6}$alkenyl, —$C_{2-6}$alkynyl and —$OC_{1-6}$alkyl. In some embodiments where the complex has the formula (c), $R^2$ is phenyl which is unsubstituted or substituted with up to 3 substituents each independently selected from the group consisting of halogen, —CN, —$NO_2$, $C_{1-6}$alkyl, —$C_{2-6}$alkenyl, —$C_{2-6}$alkynyl and —$OC_{1-6}$alkyl. In some embodiments, $R^2$ is phenyl. In some embodiments $R^2$ is styrenyl.

In some embodiments where the complex has the formula (c), each $R^a$ is independently selected from the group consisting of hydrogen, $C_{1-10}$alkyl, $C_{2-10}$alkenyl, $C_{2-10}$alkynyl, $C_{3-10}$ carbocyclyl and $C_{3-10}$ heterocyclyl, said alkyl, alkenyl, alkynyl, cycloalkyl, carbocyclyl or heterocyclyl being unsubstituted or substituted with up to 3 substituents each independently selected from the group consisting of halogen, —CN, —$NO_2$, —C(O)N($R^b$)$_2$, —C(O)$R^b$, —S(O)$_2$N($R^b$)$_2$, —C(O)O$R^b$; —$R^b$, —O$R^b$, —OC(O)$R^b$, —N($R^b$)$_2$, —N($R^b$)C(O)$R^b$ and —N($R^b$)S(O)$_2R^b$; $R^2$ is a $C_{6-10}$aromatic carbocyclyl or $C_{5-10}$ aromatic heterocyclyl, said aromatic carbocyclyl or aromatic heterocyclyl being unsubstituted or substituted with up to 3 substituents each independently selected from the group consisting of $C_{1-6}$alkyl, $C_{2-6}$ alkenyl, $C_{2-6}$alkynyl, —$OC_{1-6}$alkyl, halogen, —CN, —$NO_2$, —C(O)N($R^b$)$_2$, —C(O)$R^b$, —S(O)$_2$N($R^b$)$_2$, —C(O)O$R^b$; —$R^b$, —O$R^b$, —OC(O)$R^b$, —N($R^b$)$_2$, —N($R^b$)C(O)$R^b$ and —N($R^b$)S(O)$_2R^b$; and each $R^b$ is independently selected from the group consisting of hydrogen, $C_{1-6}$alkyl, $C_{1-6}$alkenyl, $C_{1-6}$alkynyl, $C_{3-10}$cycloalkyl, $C_{6-10}$ aromatic carbocyclyl and $C_{5-10}$ aromatic heterocyclyl, said alkyl, alkenyl, alkynyl, cycloalkyl, aromatic carbocyclyl or aromatic heterocyclyl being unsubstituted or substituted with up to 3 substituents each independently selected from the group consisting of halogen, —CN, hydroxyl, —$C_{1-6}$alkyl, —$C_{2-6}$alkenyl, —$C_{2-6}$alkynyl, —$OC_{1-6}$alkyl, —$C_{1-6}$haloalkyl, —$NH_2$, —$NHC_{1-6}$alkyl and —N($C_{1-6}$alkyl)$_2$.

In some embodiments where the complex has the formula (c), each $R^a$ is independently selected from the group consisting of hydrogen, $C_{1-10}$alkyl, $C_{2-10}$alkenyl, $C_{2-10}$alkynyl, $C_{3-10}$ carbocyclyl and $C_{3-10}$ heterocyclyl, said alkyl, alkenyl, alkynyl, cycloalkyl, carbocyclyl or heterocyclyl being unsubstituted or substituted with up to 3 substituents each independently selected from the group consisting of halogen, —CN, —NO$_2$, —C(O)N(R$^b$)$_2$, —C(O)R$^b$, —S(O)$_2$N(R$^b$)$_2$, —C(O)OR$^b$; —R$^b$, —OR$^b$, —OC(O)R$^b$, —N(R$^b$)$_2$, —N(R$^b$)C(O)R$^b$ and —N(R$^b$)S(O)$_2$R$^b$; $R^2$ is a $C_{6-10}$aromatic carbocyclyl or $C_{5-10}$ aromatic heterocyclyl, said aromatic carbocyclyl or aromatic heterocyclyl being unsubstituted or substituted with up to 3 substituents each independently selected from the group consisting of halogen, —CN, —NO$_2$, —C(O)N(R$^b$)$_2$, —C(O)R$^b$, —S(O)$_2$N(R$^b$)$_2$, —C(O)OR$^b$; —R$^b$, —OR$^b$, —OC(O)R$^b$, —N(R$^b$)$_2$, —N(R$^b$)C(O)R$^b$ and —N(R$^b$)S(O)$_2$R$^b$; and each R$^b$ is independently selected from the group consisting of hydrogen, $C_{1-6}$alkyl, $C_{1-6}$alkenyl, $C_{1-6}$alkynyl, $C_{3-10}$cycloalkyl, $C_{6-10}$ aromatic carbocyclyl and $C_{5-10}$ aromatic heterocyclyl, said alkyl, alkenyl, alkynyl, cycloalkyl, aromatic carbocyclyl or aromatic heterocyclyl being unsubstituted or substituted with up to 3 substituents each independently selected from the group consisting of halogen, —CN, hydroxyl, —C$_{1-6}$alkyl, —C$_{2-6}$alkenyl, —C$_{2-6}$alkynyl, —OC$_{1-6}$alkyl, —C$_{1-6}$haloalkyl, —NH$_2$, —NHC$_{1-6}$alkyl and —N(C$_{1-6}$alkyl)$_2$. In some embodiments where the complex has the formula (c), each $R^a$ is selected from the group consisting of hydrogen, $C_{1-6}$alkyl, $C_{6-10}$ aromatic carbocyclyl and $C_{5-10}$ aromatic heterocyclyl, said aromatic carbocyclyl or aromatic heterocyclyl being unsubstituted or substituted with up to 3 substituents selected from the group consisting of halogen, —CN, —NO$_2$, —C$_{1-6}$alkyl, —C$_{2-6}$alkenyl, —C$_{2-6}$alkynyl and —OC$_{1-6}$alkyl; and $R^2$ is $C_{6-10}$ aromatic carbocyclyl or $C_{5-10}$ aromatic heterocyclyl, said aromatic carbocyclyl or aromatic heterocyclyl being unsubstituted or substituted with up to 3 substituents each independently selected from the group consisting of halogen, —CN, —NO$_2$, C$_{1-6}$alkyl, —C$_{2-6}$alkenyl, —C$_{2-6}$alkynyl and —OC$_{1-6}$alkyl. In some embodiments where the complex has the formula (c), each $R^a$ is selected from the group consisting of hydrogen, $C_{1-6}$alkyl, or phenyl, said phenyl being unsubstituted or substituted with one —NO$_2$ group or one —OMe group; and $R^2$ is unsubstituted phenyl. In some embodiments where the complex has the formula (c), each $R^a$ is selected from the group consisting of hydrogen, $C_{1-6}$alkyl, or phenyl, said phenyl being unsubstituted or substituted with one —NO$_2$ group or one —OMe group; and $R^2$ is styrenyl.

In some embodiments the organobismuth (III) phosphinate complex of the present disclosure has a structure comprising formula (d):

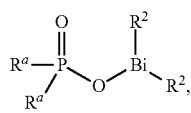

(d)

wherein each $R^2$ is independently an aromatic carbocyclyl or aromatic heterocyclyl group. In some embodiments the organobismuth (III) phosphinate complex has a structure consisting of formula (d). The definitions for the $R^a$ and $R^2$ groups in the complex of formula (d) are as defined above with respect to formulae (a), (b) and (c). In some embodiments, each $R^a$ is selected from the group consisting of hydrogen, $C_{1-6}$alkyl, or phenyl, said phenyl being unsubstituted or substituted with one —NO$_2$ group or one —OMe group. In some embodiments, each $R^2$ is phenyl or styrenyl. In some embodiments where the complex has the formula (d), each $R^a$ is selected from the group consisting of hydrogen, $C_{1-6}$alkyl, or phenyl, said phenyl being unsubstituted or substituted with one —NO$_2$ group or one —OMe group; and each $R^2$ is unsubstituted phenyl or styrenyl. In some embodiments where the complex has the formula (d), each $R^a$ is independently selected from the group consisting of hydrogen, $C_{1-10}$alkyl, $C_{2-10}$alkenyl, $C_{2-10}$alkynyl, $C_{3-10}$ carbocyclyl and $C_{3-10}$ heterocyclyl, said alkyl, alkenyl, alkynyl, cycloalkyl, carbocyclyl or heterocyclyl being unsubstituted or substituted with up to 3 substituents each independently selected from the group consisting of halogen, —CN, —NO$_2$, —C(O)N(R$^b$)$_2$, —C(O)R$^b$, —S(O)$_2$N(R$^b$)$_2$, —C(O)OR$^b$; —R$^b$, —OR$^b$, —OC(O)R$^b$, —N(R$^b$)$_2$, —N(R$^b$)C(O)R$^b$ and —N(R$^b$)S(O)$_2$R$^b$; each $R^2$ is independently a $C_{6-10}$aromatic carbocyclyl or $C_{5-10}$ aromatic heterocyclyl, said aromatic carbocyclyl or aromatic heterocyclyl being unsubstituted or substituted with up to 3 substituents each independently selected from the group consisting of $C_{1-6}$alkyl, $C_{2-6}$ alkenyl, $C_{2-6}$alkynyl, —OC$_{1-6}$alkyl, halogen, —CN, —NO$_2$, —C(O)N(R$^b$)$_2$, —C(O)R$^b$, —S(O)$_2$N(R$^b$)$_2$, —C(O)OR$^b$; —R$^b$, —OR$^b$, —OC(O)R$^b$, —N(R$^b$)$_2$, —N(R$^b$)C(O)R$^b$ and —N(R$^b$)S(O)$_2$R$^b$; and each R$^b$ is independently selected from the group consisting of hydrogen, $C_{1-6}$alkyl, $C_{1-6}$alkenyl, $C_{1-6}$alkynyl, $C_{3-10}$cycloalkyl, $C_{6-10}$ aromatic carbocyclyl and $C_{5-10}$ aromatic heterocyclyl, said alkyl, alkenyl, alkynyl, cycloalkyl, aromatic carbocyclyl or aromatic heterocyclyl being unsubstituted or substituted with up to 3 substituents each independently selected from the group consisting of halogen, —CN, hydroxyl, —C$_{1-6}$alkyl, —C$_{2-6}$alkenyl, —C$_{2-6}$alkynyl, —OC$_{1-6}$alkyl, —C$_{1-6}$haloalkyl, —NH$_2$, —NHC$_{1-6}$alkyl and —N(C$_{1-6}$alkyl)$_2$.

In some embodiments, the organobismuth (III) complexes of the present disclosure do not comprise a tridentate moiety containing three groups bonded to the bismuth. In some embodiments, $R^2$ is not a 2,6-bis[(dimethylamino)methyl]phenyl group. The organobismuth (III) phosphinate complex of the present disclosure is not 2,6-(Me$_2$NCH$_2$)C$_6$H$_3$Bi[OP(H)(O)Ph]$_2$ or 2,6-(Me$_2$NCH$_2$)$_2$C$_6$H$_3$Bi[OP(O)(Ph)$_2$]$_2$, i.e. it is not

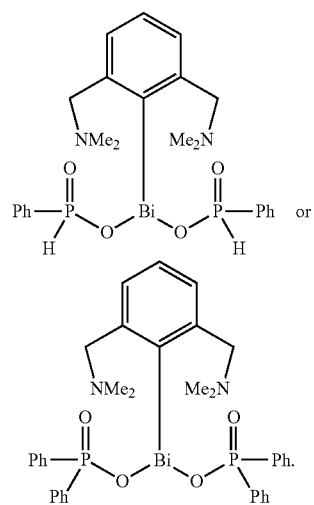

The organobismuth (III) phosphinate complexes described herein may include salts, solvates, hydrates, isomers, tautomers, racemates, stereoisomers, enantiomers or diastereoisomers of those complexes. Asymmetric centers may exist in the complexes disclosed herein. These centers can be designated by the symbols "R" or "S," depending on the configuration of substituents around the chiral carbon atom. It should be understood that the present disclosure encompasses all stereochemical isomeric forms, including diastereomeric, enantiomeric, and epimeric forms, as well as D-isomers and L-isomers, and mixtures thereof. Additionally, the complexes disclosed herein may exist as geometric isomers. The present invention includes all cis, trans, syn, anti, entgegen (E), and zusammen (Z) isomers as well as the appropriate mixtures thereof. Additionally, complexes may exist as tautomers; all tautomeric isomers are provided by this invention.

Where the organobismuth (III) complex has a net overall charge, for example where the $R^1$, $R^2$ or $R^3$ group contains a substituent such as a carboxyl or amino group, the organobismuth (III) complex may be present in the form of a salt. In principle the counterion may be any organic or inorganic moiety that stabilizes the charge on the parent complex.

Additionally, the organobismuth (III) phosphinate complexes disclosed herein may exist in unsolvated as well as solvated forms. Polymorphic forms of the complexes are also encompassed.

Products, Devices, Materials and Compositions

As discussed above, a series of organobismuth (III) phosphinate complexes have been identified which, unlike structurally related tris(phosphinate)bismuth(III) complexes, unexpectedly have good antibacterial properties. The complexes have been demonstrated to have activity against both gram-positive and gram-negative bacteria, and have shown activity against MRSA and VRE. Bismuth is also known to have much lower toxicity to living organisms than some other heavy metals such as lead, and has been substituted for lead in manufacturing industries (N Yang and H Sun, Bismuth: Environmental Pollution and Health Effects, In Nriagu J O (Ed.), Encyclopedia of Environmental Health, p. 414-420, Burlington, UK, Elsevier, 2011). As a result, the combination of good antibacterial activity together with lower general toxicity of bismuth makes the organobismuth (III) phosphinate complexes of the present disclosure particularly suitable for use as additives in products, materials and the like where antibacterial properties are desirable. In addition, example organobismuth (III) phosphinate complexes of the present disclosure have been found to be stable to both moisture and temperature, and to have low solubility in organic and aqueous solvents. Thus in some embodiments the organobismuth (III) phosphinate complex has a half-life (i.e. the time taken for 50% of the complex to be converted to a different species) in water at 25° C. of at least 24 hours, at least 48 hours, at least 72 hours, at least 1 week, at least 2 weeks, at least 1 month, at least 2 months, at least 3 months, at least 6 months, or at least 1 year. In some embodiments the organobismuth (III) phosphinate complex is thermally stable upon heating to at least 100° C., at least 125° C., at least 150° C., at least 175° C., at least 200° C., or at least 225° C. In some embodiments the organobismuth (III) phosphinate complex has an aqueous solubility at 25° C. of less than 10 g/l, less than 1 g/l, less than 0.5 g/l, less than 0.2 g/l, less than 0.1 g/l, less than 0.05 g/l, less than 0.02 g/l, or less than 0.01 g/l. In some embodiments the organobismuth(III) phosphinate complex has a solubility in dimethyl sulfoxide (DMSO) at 25° C. of less than 10 g/l, less than 1 g/l, less than 0.5 g/l, less than 0.2 g/l, less than 0.1 g/l, less than 0.05 g/l, less than 0.02 g/l, or less than 0.01 g/l.

In some embodiments, the organobismuth (III) phosphinate complexes may be present in the form of small particles, e.g. nanoparticles. Without wishing to be bound by any theory, it is considered that the antibacterial properties of the complexes may be improved where the complex is present in a form such that surface area is maximised, particularly where solubility of the complex is low, in order to maximise contact of complex with bacteria. Thus, in some embodiments the organobismuth (III) phosphinate complex is present in particulate form wherein the particles have a mean diameter of less than 1000 μm, less than 500 μm, less than 200 μm, less than 100 μm, less than 50 μm, less than 20 μm, less than 10 μmm, less than 5 μm, less than 2 μm, or less than 1 μm. In some embodiments the organobismuth (III) phosphinate complex is present in particulate form wherein the particles have a mean diameter in the range of from 1000 μm to 500 μm, from 500 μm to 200 μm, from 200 μm to 100 μm, from 100 μm to 50 μm, from 50 μm to 20 μm, from 20 μm to 10 μm, from 10 μm to 5 μm, from 5 μm to 2 μm, or from 2 μm to 1 μm.

The organobismuth (III) complexes may be used as antibacterial additives for coating surfaces of products, or for dispersal within products (e.g. polymeric products) in a variety of applications. Based on the stability and solubility properties exhibited by the example complexes, the organobismuth (III) phosphinate complexes are also expected to be long-lasting, have low levels of degradation and low levels of leaching. Accordingly, the present disclosure also provides a product, device, material or composition comprising a complex as defined above.

In some embodiments the complex is distributed within the product, device, material or composition. For example, the composition may be a curable composition. A curable composition is a composition which is capable of being hardened or fixed, for example by exposure of a composition to high temperature, exposure to light (e.g. UV light) or exposure to atmospheric conditions (e.g. compositions which cure or harden as a result of reaction with moisture present in the atmosphere). In some embodiments, the curable composition may be one which cures by virtue of evaporation of solvent present in the composition. In some embodiments, the curable compositions may be one which cures by virtue of a chemical reaction taking place between components present in the composition (e.g. on exposure to high temperature, or to UV light) and/or between components present in the composition and substances present in the surrounding environment (e.g. atmospheric water). The curable composition comprising the organobismuth (III) phosphinate complex may for example be a one-part composition (e.g. a composition which cures/hardens on exposure to atmospheric conditions, UV light, or heat). Alternatively, in cases where the composition is prepared by mixing together multiple precursor compositions (e.g. a first composition comprising polymers or prepolymers, and a second composition comprising cross-linker or hardener) which cure by virtue of a chemical reaction taking place between components present in the different compositions upon admixing, the organobismuth (III) phosphinate may for example be present in one of the precursor compositions. Examples of curable compositions include adhesive compositions, such as cement compositions. Further examples include sealant compositions. The composition may for example be a coating composition for coating the surface of an object, e.g. a composition comprising a film former/binder, organobismuth (III) phosphinate complex, and optionally other components such as diluent, pigment, and/or filler. The composition may for example be a monomer composition comprising a polymerisable monomer which is intended for polymerisation to produce a polymerised, plastic, product, and which contains the complex as an antibacterial additive.

The product, device, material or composition may be a polymeric material comprising an organobismuth (III) phosphinate complex. For example, the complex may be dispersed as a separate component within the bulk of the polymeric material. Alternatively, where for example the polymeric material is produced by carrying out polymerisation in the presence of an organobismuth (III) phosphine complex which itself has a polymerisable group such as an alkenyl group (e.g. where $R^2$ is a styrene group), the complex may be present in the polymeric material as an integral part of the polymer (i.e. covalently bound to the polymer).

As an alternative to the complex being dispersed within a product, a product may be coated with an antibacterial surface coating comprising the complex. For example, the exterior of a product may be covered by spraying or coating with a composition comprising the complex. In some embodiments, for example where the complex is for use in an antibacterial coating composition for covering the surface of an object, and where the organobismuth (III) phosphinate complex has low solubility, the composition may take the form of a suspension composition comprising the complex suspended in a liquid carrier.

The amount of the organobismuth (III) phosphinate complexes used in products, compositions and the like will depend on the nature of the material and the intended application. In some embodiments, the complex is present in an amount of up to 25, up to 20, up to 15, up to 10, up to 5, up to 2, up to 1, up to 0.5, up to 0.2, up to 0.1, up to 0.05, up to 0.02. up to 0.01, up to 0.005, up to 0.002, or up to 0.001% by weight of the product, material, device or composition which comprises the complex.

The antibacterial properties of the organobismuth (III) phosphinate complexes make them particularly suitable for use in the hospital/medical environment. Accordingly, in some embodiments the product, device, material or composition comprising the complex is a medical product, device, material or composition, such as a wound dressing, a suture, a surgical implement or a medical implant. For example sutures or stitches (e.g. stitches formed of polymers having glycolic acid and/or lactic acid monomer units, such as polygalactin 910) may be coated with a coating composition comprising the organobismuth (III) phosphinate complex, or the stitches formed from monomer compositions containing the complex. Surgical equipment and implements, and medical implants such as dental implants, stents and components used in joint arthroplasty, may be coated with a coating composition comprising the organobismuth (III) phosphinate complex or, where appropriate, formed of a composition comprising the complex. The organobismuth (III) phosphinate may also or alternatively find use in wound dressings. For example the product may be a wound dressing comprising a woven material made of synthetic and/or natural polymer (e.g. polyurethane, polyester, cotton) coated or impregnated with a composition comprising the complex, or, in the case of a synthetic polymer, formed of a monomer composition containing the complex. The medical product, device, composition or material comprising the complex may also be a curable medical adhesive (e.g. a cyanoacrylate composition), a bone or dental cement (e.g. methyl methacrylate/polymethyl methacrylate compositions), a dental primer or dental adhesive. Medical consumables where antibacterial properties are desirable, such as disposable gloves or masks, may also comprise the organobismuth (III) phosphinate complex. Alternatively or in addition, the complex may be used to prevent spread of microbes (e.g. bacteria) in the hospital environment via objects whose surfaces are commonly contacted by humans, such as door handles, desks, bedside cabinets, worktops and the like. For example those objects may be coated with a coating composition comprising the organobismuth (III) phosphinate complex.

The organobismuth (III) phosphinate complexes may also find use in sterile packaging applications, e.g. for packaging of sterile consumables such as syringes, needles, gloves, surgical implements, medical devices. Accordingly, in some embodiments the product, device, material or composition is or comprises antibacterial packaging comprising the complex. Such packaging may for example be made of paper-based and/or polymer-based materials coated with and/or impregnated with the organobismuth (III) phosphinate complex.

In some embodiments, the product, device, material or composition is a cellulosic material (a material containing a cellulose or derivative thereof) comprising the organobismuth (III) phosphinate complex. For example it may be a cellulosic paper-based material (e.g. paper, tissue, card). In another example, it may be a cellulosic dressing or bandage. In some embodiments it may be a cellulosic packaging material.

As discussed above, the organobismuth (III) phosphinate complexes may be used to impart antibacterial properties to a variety of medical products. For example wound dressings coated or impregnated with the complex may be applied to the skin of a patient to prevent infection, or the antibacterial complex may be present in a bone cement composition to prevent infection following joint replacement surgery. Thus organobismuth (III) complexes of the present disclosure, and compositions comprising the complexes, find use in the prevention and or treatment of bacterial infections. Accordingly, provided herein is an organobismuth (III) phosphinate complex as defined above, or a composition comprising the complex, for use in therapy. Also provided herein is a method of treating or preventing a disease or disorder in a subject, comprising administering to the subject a therapeutically effective amount of an organobismuth (III) phosphinate complex as defined in above, or of a composition comprising the complex. Also provided herein is a pharmaceutical agent comprising a complex as defined above. Where the complex is administered in the form of a composition, such as bone cement or dental cement, the additional components of the composition, such as carrier and/or filler, will be selected so as to be acceptable for administration to a patient. The organobismuth (III) phosphinate complexes disclosed herein find use in the treatment and/or prevention of a bacterial infection or a condition associated with a bacterial infection. In some embodiments the complexes are for use in the treatment and/or prevention of a wound infection. In some embodiments the complexes are for use in the prevention and/or treatment of an infection caused by a gram-positive bacteria. In some embodiments the complexes are for use in the prevention and/or prevention of an infection caused by a gram-negative bacteria. In some embodiments the complexes are for use in the treatment and/or prevention of an infection caused by a bacteria selected from the group consisting of *Staphylococcus aureus* (e.g. methicillin-resistant *Staphylococcus aureus*), *Escherichia coli* and vancomycin-resistant *Enterococcus*. Also provided herein is a method of treating or preventing a bacterial infection or a condition associated with a bacterial infection in a subject, comprising administering to the subject a therapeutically effective amount of an organobismuth (III) phosphinate as defined above. Also provided herein is use of an organobismuth (III) phosphinate complex as defined above for the manufacture of a medicament for the prevention or treatment of a bacterial infection or a condition associated with a microbial infection. Also provided herein is use of an organobismuth (III) phosphinate complex as defined above, for the prevention and/or treatment of a bacterial infection or a condition associated with a bacterial infection. The subject to whom the complex is administered may be an animal, for example a mammal. In some embodiments, the subject is a human. In another embodiments, the subject is a non-human animal.

Also provided herein is use of an organobismuth (III) phosphinate complex as defined above, or a product, material, device or composition comprising the complex, for preventing bacterial spread. In some embodiments, the organobismuth (III) phosphinate complex is not used on a human or animal body, e.g. it is used ex vivo, in or on products and materials in the environment so as to reduce or prevent establishment and spread of microbes.

The organobismuth (III) phosphinate complexes may also find use in applications outside the medical environment. For example, the complex may find use in products, devices, materials or compositions used in building construction, renovation and/or maintenance, e.g. in bathroom or kitchen environments where reduction of bacterial spread is particularly desirable. Examples of compositions which may comprise the organobismuth (III) complex as an antibacterial additive include curable and/or polymerisable compositions, such as coating compositions (e.g. lacquer compositions, varnish compositions, or paint compositions comprising a binder or film-former, and optionally other components such as pigment and/or diluent), adhesive or sealant compositions (e.g. a silicone or polyurethane sealant composition), cement compositions (e.g. a Portland-type cement composition comprising calcium silicates), concrete (e.g. compositions comprising cement, aggregates and water), or grout, mortar or stucco compositions (e.g. compositions comprising water, cement and sand).

Preparation of Organobismuth (III) Phosphinate Complexes

The following process can be used to prepare organobismuth (III) phosphinate complexes of the present disclosure:
(i) reacting an organobismuth complex of formula (d):

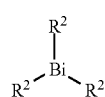

(d)

wherein $R^2$ is as defined above, with a phosphinic acid of formula (e):

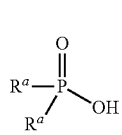

(e)

wherein each $R^a$ is as defined above, to produce the organobismuth (III) phosphinate complex. The reaction is typically carried out in the presence of a polar organic solvent such as ethanol or DMSO, and may for example be carried out at elevated temperature. In the complex of formula (d), preferably $R^2$ is $C_{6-10}$ aromatic carbocyclyl or $C_{5-10}$ aromatic heterocyclyl, said aromatic carbocyclyl or aromatic heterocyclyl being unsubstituted or substituted with up to 3 substituents each independently selected from the group consisting of halogen, —CN, —NO$_2$, $C_{1-6}$alkyl, —C$_{2-6}$alkenyl, —C$_{2-6}$alkynyl and —OC$_{1-6}$alkyl. In the phosphinic acid of formula (e), preferably $R^a$ is hydrogen, $C_{1-6}$ alkyl, $C_{6-10}$ aromatic carbocyclyl or $C_{5-10}$ aromatic heterocyclyl, said aromatic carbocyclyl or aromatic heterocyclyl being unsubstituted or substituted with up to 3 substituents selected from the group consisting of halogen, —CN, —NO$_2$, —C$_{1-6}$alkyl, —C$_{2-6}$alkenyl, —C$_{2-6}$alkynyl and —OC$_{1-6}$alkyl.

The synthetic process described above allows organobismuth (III) phosphinate complexes to be obtained reproducibly in high yield, with no further purification being required in many cases.

The present disclosure is further described by the following examples. It is to be understood that the following description is for the purpose of describing particular embodiments only and is not intended to be limiting with respect to the above description.

Synthesis of bismuth (III) phosphinate Complexes

General Procedure 1: Synthesis of organobismuth (III) phosphinate Complexes

Triphenylbismuth (1 eq.) and the appropriate phosphinic acid (3 eq.) were heated at reflux in ethanol (unless otherwise stated), for four hours. The final product was collected by gravity filtration and washed with hot ethanol and diethyl ether to yield the desired bismuth phosphinate complex of the type Bi(R$^1$)$_2$R$^2$.

General Procedure 2: Synthesis of Comparative Examples

All reactions were carried out under standard Schlenk conditions using tetrahydrofuran (THF). [Bi(O$^t$Bu)$_3$] (1 eq.) dissolved in THF was added to a THF solution (or suspension) of the phosphinic acid (3 eq.) which was already cooled to −80° C. This temperature was maintained for approximately one hour and subsequently warmed to room temperature while stirring overnight. The final product was collected by gravity filtration and washed with hot ethanol and diethyl ether to yield the desired bismuth phosphinate complex of the type Bi(R$^1$)$_3$.

Preparation of phosphinic acid (Ligand)

Phosphinic acid ligands were either obtained from commercial sources (e.g. Sigma-Aldrich®) or prepared as discussed below.

Bis(3-nitrophenyl)phosphinic acid

The synthesis was adapted from previously published methods (J. F. Bunnet, K. Tetsuzo, N. S. Nudelman, J. Org. Chem., 1969, 34, 4.). Diphenylphosphinic acid (0.712 g, 3.26 mmol) was slowly added to a solution of concentrated HNO$_3$ (2 mL) and concentrated H$_2$SO$_4$ (4 mL) stirring in an ice bath. After the addition, the yellow solution was allowed to at room temperature overnight. The reaction was poured over ice to yield a white precipitate in a yellow solution. The solid was collected by filtration over a frit and washed with water until the filtrate became colourless. Yield: 0.442 g, 44%, M.p. ° C. 268. (Lit 265° C., dec) (R. M. Perez, J. K. W. Sandler, V. Altstädt, et al, *J. Appl. Polym. Sci.,* 2007, 105, 5). $^1$H NMR (δ, ppm, DMSO-d$_6$): 8.51 (2H, d, J=12.4 Hz, CH), 8.38 (2H, d, J=8 Hz, N—C—CH—CH), 8.19 (2H, t, J=9.4 Hz, P—C—CH—CH), 7.79 (2H, td, J=8, 3.2 Hz, N—C—CH—CH). $^{13}$C NMR (δ, ppm, DMSO-d$_6$): 147.7 ($J_{CP}$=15 Hz, N—C), 137.4 ($J_{CP}$=10 Hz, P—C—CH—CH), 136.6 ($J_{CP}$=135 Hz, C—P), 130.7 ($J_{CP}$=13 Hz, N—C—CH—CH), 126.51 ($J_{CP}$=2.6 Hz, N—C—CH—CH), 125.4 ($J_{CP}$=11 Hz, C—CH—C) $^{31}$P NMR (δ, ppm, DMSO-d$_6$): 17.69. ESI-MS$^-$ (solvent; DMSO): m/z=307 (100%, C$_{12}$H$_8$N$_2$PO$_6^-$).

EXAMPLE COMPLEXES 1 TO 5

Example 1: Phenyl bismuth bis(diphenylphosphinate)

Example 1 was prepared in accordance with general procedure 1 using diphenylphosphinic acid. Yield: 0.140 g, 69%, Elemental analysis for C$_{30}$H$_{25}$BiO$_4$P$_2$: Calculated: C, 50.01, H, 3.50. Found: C, 49.72, H, 3.45 (A120) $v_{max}$ (FT-IR)/cm$^{-1}$ 3052 w, 2114 w, 1892 w, 1819 w, 1473 w, 1436 m, 1180 w, 1127 s, 1096 s, 1066 m, 1033 s, 1012 s, 993 s, 851 w, 755 m, 725 s, 692 s. $^{13}$C CP-MAS (δ, ppm): 138.9, 131.3, 129.2. $^{31}$P HPDEC-MAS (δ, ppm): 20.47.

Example 2: Phenyl bismuth bis(bis(4-methoxyphenyl)phosphinate)

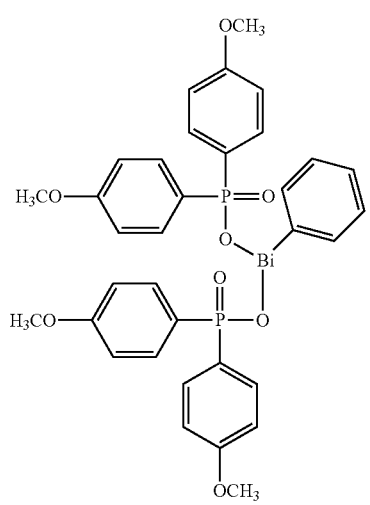

Example 2 was prepared in accordance with general procedure 1 using bis(4-methoxyphenyl)phosphinic acid. Yield: 0.197 g, 62%, Elemental analysis for C$_{34}$H$_{33}$BiO$_8$P$_2$: Calculated: C, 48.58, H, 3.96. Found: C, 48.72, H, 3.84. $v_{max}$ (FT-IR)/cm$^{-1}$ 3054 w, 2834 w, 2548 w, 2108 w, 2007 w, 1593 m, 1568 m, 1500 m, 1474 m, 1431 m, 1289 m, 1243 s, 1179 m, 1121 s, 1091 s, 1015 s, 992 s, 909 w, 829 s, 803 s, 726 s. $^{13}$C CP-MAS (δ, ppm): 161.3, 136.8, 131.7, 129.1, 127.2, 123.9, 118.1, 112.1, 110.3. $^{31}$P HPDEC-MAS (δ, ppm): 23.74.

Example 3: Phenyl bismuth bis(bis(3-nitrophenyl)phosphinate) [3]

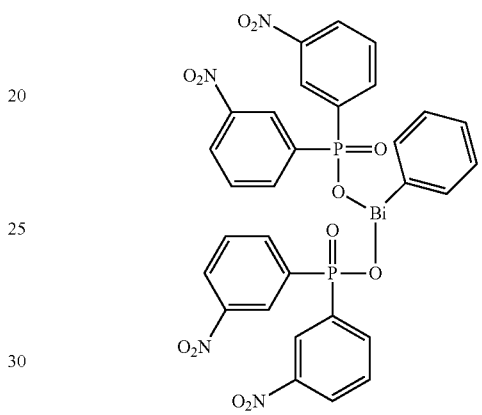

Example 3 was prepared in accordance with general procedure 1 using bis(3-nitrophenyl)phosphinic acid. Yield: 0.165 g, 88%, Elemental analysis for C$_{30}$H$_{21}$BiN$_4$O$_{12}$P$_2$: Calculated: C, 40.02, H, 2.35, N, 6.22. Found: C, 40.36, H, 2.32, N, 6.10. $v_{max}$ (FT-IR)/cm$^{-1}$ 2227 w, 1608 m, 1531 s, 1472 w, 1430 w, 1346 s, 1304 w, 1277 w, 1202 w, 1132 s, 1073 m, 1028 s, 996 m, 916 w, 876 m, 809 m, 770 m, 736 m. $^{13}$C CP-MAS (δ, ppm): 148.6, 147.1, 138.3, 130.3, 126.9. $^{31}$P HPDEC-MAS (δ, ppm): 15.52.

Example 4: Phenyl bismuth bis(phenylphosphinate)

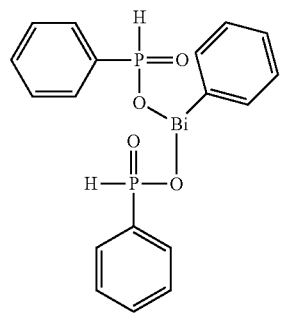

Example 4 was prepared in accordance with general procedure 1 using phenylphosphinic acid. Yield: 0.130 g, 78%, Elemental analysis for C$_{18}$H$_{17}$BiO$_4$P$_2$: Calculated: C, 38.05, H, 3.02. Found: C, 38.01, H, 2.97. $v_{max}$ (FT-IR)/cm$^{-1}$ 3058 w, 2366 w, 2338 w, 2110 w, 1891 w, 1812 w, 1591 w, 1475 w, 1438 m, 1429 m, 1135 m, 1091 s, 1034 m, 1015 s, 970 s, 861 w, 747 s, 726 s, 707 m, 689 w. $^{13}$C CP-MAS (δ, ppm): 140.5, 132.0, 130.7, 127.2. $^{31}$P HPDEC-MAS (δ, ppm): 20.05, 13.64.

Example 5: Phenyl Bismuth bis(dimethylphosphinate)

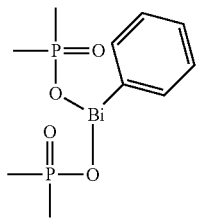

Example 5 was prepared in accordance with general procedure 1 using dimethylphosphinic acid and dimethylsulfoxide (DMSO) as the solvent. Yield: 0.063 g, 57%, Elemental analysis for $C_6H_{18}BiO_6P_3$: Calculated: C, 25.44, H, 3.63. Found: C, 25.48, H, 3.57 $ν_{max}$ (FT-IR)/cm$^{-1}$ 3052 w, 2982 w, 2916 w, 2344 w, 2114 w, 2086 w, 1475 w, 1429 w, 1415 w, 1293 m, 1290 m, 1144 m, 1083 m, 1061 m, 1017 s, 913 w, 860 s, 730 s, 689 s. $^{13}$C CP-MAS (δ, ppm): 176.3, 43.5. $^{31}$P HPDEC-MAS (δ, ppm): 46.3 (sh), 42.4.

Example 5a: ((Bis(4-vinylphenyl)bismuthanyl)oxy)diphenylphosphine oxide

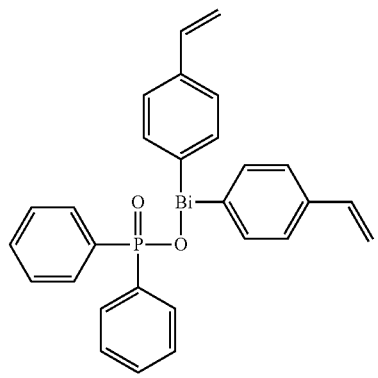

Example 5a was prepared by in accordance with general procedure 1 using tris(4-vinylphenyl)bismuthane (1 eq.) and diphenylphosphinic acid (3 eq.) at room temperature in ethanol. Yield: 38%. Elemental analysis for $C_{28}H_{24}BiO_2P$: Calculated: C, 53.18, H, 3.83. Found: C, 53.14, H, 3.77. $^1$H NMR (δ, ppm, DMSO-$d_6$): 8.26 (4H, d, J=10 Hz, Bi-Ph-CH=CH$_2$), 7.66 (4H, d, J=5 Hz, Bi-Ph-CH=CH$_2$), 7.56 (4H, t, J=10 Hz, Bi—P=OO—(Ph)$_2$), 7.37-7.29 (6H, m, Bi—P=OO—(Ph)$_2$), 6.69 (2H, q, J=10 Hz, Bi-Ph-CH=CH$_2$), 5.84 (2H, d, J=20 Hz, Bi-Ph-CH=CH$_2$), 5.25 (2H, d, J=10 Hz, Bi-Ph-CH=CH$_2$).

COMPARATIVE EXAMPLES

Comparative Example 6: Bismuth tris(diphenylphosphinate)

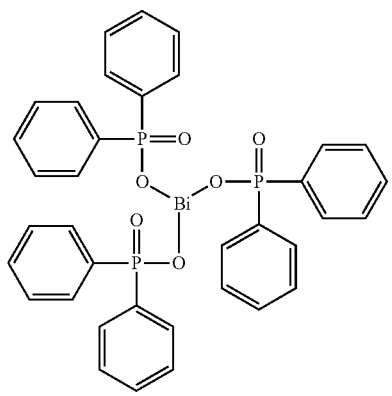

Comparative example 6 was prepared in accordance with general procedure 2 using diphenylphosphinic acid. Yield: 0.282 g, 69%, Elemental analysis for $C_{36}H_{30}BiO_6P_3$: Calculated: C, 50.25, H, 3.51. Found: C, 50.26, H, 3.56 (A123). $ν_{max}$ (FT-IR)/cm$^{-1}$ 3051 w, 2113 w, 2058 w, 1906 w, 1591 w, 1484 w, 1436 m, 1256 w, 1183 w, 1122 m, 1091 s, 1066 m, 1031 s, 1009 s, 990 s, 746 m, 728 s. $^{13}$C CP-MAS (δ, ppm): 142.2, 135.0, 133.3, 130.1, 127.3. $^{31}$P HPDEC-MAS (δ, ppm): 24.22

Comparative Example 7. Bismuth tris(bis(4-methoxyphenyl)phosphinate)

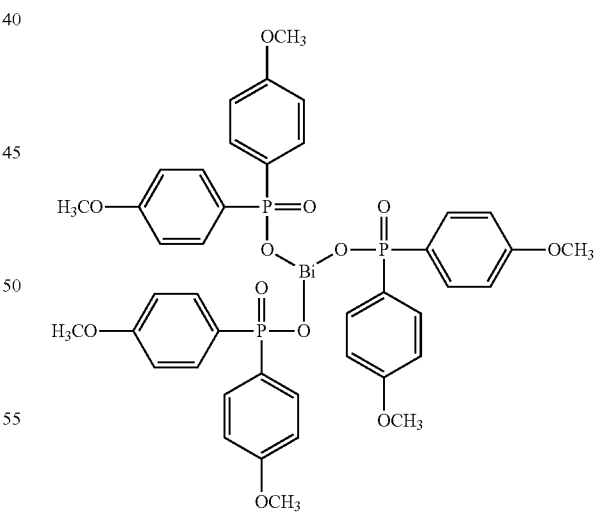

Comparative example 7 was prepared in accordance with general procedure 2 using bis(4-methoxyphenyl)phosphinic acid. Yield: 0.393 g, 76%, Elemental analysis for $C_{42}H_{42}BiO_{12}P_3$: Calculated: C, 48.47, H, 4.07. $ν_{max}$ (FT-IR)/cm$^{-1}$ 3064 w, 3002 w, 2950 w, 3901 w, 2834 w, 2544 w, 2299 w, 2105 w, 1595 m, 1570 m, 1500 m, 1458 m, 1403 w, 1292 m, 1248 m, 1178 m, 1122 s, 1082 s, 993 s, 986 s, 827 s, 800 s, 722 s, 668 s. $^{13}$C CP-MAS (δ, ppm): 137.4, 135.9, 133.3, 131.3, 126.6, 124.7. $^{31}$P HPDEC-MAS (δ, ppm): 23.82.

Comparative Example 8: Bismuth tris(bis(3-nitrophenyl)phosphinate)

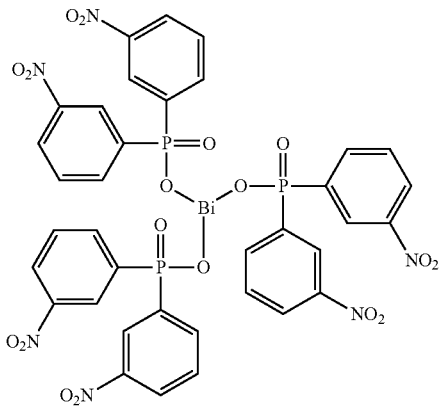

Comparative example 8 was prepared in accordance with general procedure 2 using bis(3-nitrophenyl)phosphinic acid. Yield: 0.253 g, 87%, Elemental analysis for $C_{36}H_{24}BiN_6O_{18}P_3$: Calculated: C, 38.25, H, 2.14, N, 7.43. Found: C, 38.04, H, 2.09, N, 7.19. $v_{max}$ (FT-IR)/cm$^{-1}$ 3082 w, 2869 w, 2113 w, 1608 m, 1575 m, 1525 s, 1470 w, 1421 w, 1348 s, 1305 w, 1277 w, 1173 w, 1146 w, 1091 s, 1073 s, 1017 s, 992 s, 904 w, 880 m, 811 m, 767 m, 729 s, 676 s, 662 s. $^{13}$C CP-MAS (δ, ppm): 148.4, 136.6, 129.8, 126.4. $^{31}$P HPDEC-MAS (δ, ppm): 19.26.

Comparative Example 9. Bismuth tris(phenylphosphinate)

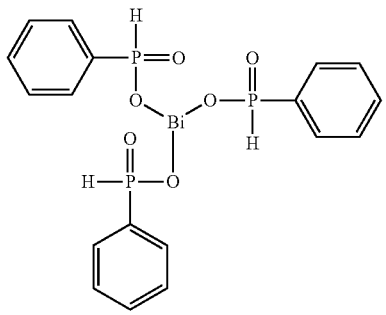

Comparative example 9 was prepared in accordance with general procedure 2 using phenylphosphinic acid. Yield: 0.22 g, 67%, Elemental analysis for $C_{18}H_{18}BiO_6P_3$: Calculated: C, 34.20, H, 2.87. Found: C, 34.39, H, 2.93. $v_{max}$ (FT-IR)/cm$^{-1}$ 3143 w, 3074 w, 3049 w, 2377 w, 2113 w, 1897 w, 1591 w, 1482 w, 1436 m, 1377 w, 1309 w, 1211 w, 1185 w, 1098 s, 1031 s, 1016 s, 974 (924 sh) s, 740 s, 705 s, 688 s. $^{13}$C CP-MAS (δ, ppm): 136.9, 133.1, 130.9, 128.9, 127.8, 126.3. $^{31}$P HPDEC-MAS (δ, ppm): 17.28.

Comparative Example 10: Bismuth tris(dimethylphosphinate)

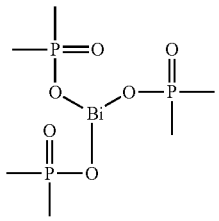

Comparative example 10 was prepared in accordance with general procedure 2 using dimethylphosphinic acid. IR (B25): $v_{max}$ (FT-IR)/cm$^{-1}$ 2986 w, 2919 w, 2120 w, 1928 w, 1647 w, 1425 w, 1299 m, 1290 m, 1200 w, 1080 s, 1013 s, 863 s, 742 m, 713 w.

Antibacterial Testing Against Gram-Negative and Gram-Positive Bacteria

Antimicrobial testing was carried out on the series of complexes synthesised. The first testing was conducted against the gram-negative bacteria *E. coli* and the gram-positive bacteria *S. aureus*. The organobismuth (III) phosphinate complexes demonstrated excellent activity against both gram-positive and gram-negative bacteria. This is surprising given that gram-positive and gram-negative bacteria have different cell-wall/cell-membrane characteristics, and typically display different sensitivity profiles to the same antibacterial agent. Thus the organobismuth (III) phosphinate complexes of the present disclosure may be viewed as broad spectrum antibacterial agents, having good general activity against different bacteria types.

Test 1

Bacteria were grown in 40 mL Lysogeny broth (LB), shaking at 37° C. to an optical density (OD) of 0.6 (2-3 hr). The culture was divided in two, 5 mL cultures. One of the cultures was used as a control, containing no organobismuth (III) phosphinate complex. To the other culture, 10 mg of the appropriate organobismuth (III) phosphinate complex was added. The control and organobismuth(III) phosphinate complex-containing cultures were then incubated for 2 hours at 37° C. with shaking. An aliquot was removed from each culture, serially diluted and 50 uL spread on lysogeny broth plates (~1 in 10$^7$ gives countable colony numbers for the wild type controls). The plates were incubated overnight at 37° C. The colonies were counted and multiplied by the dilution factor to determine the colony-forming unit (cfu)/ml of the original culture. The results of the tests against *E. coli* and *S. aureus* are shown in Tables 1a and 1b.

TABLE 1a

Organobismuth complexes and the corresponding ligands tested against *E. coli* and *S. aureus*.

| Bismuth Complex | Colony | |
|---|---|---|
| | *E. coli* | *S. aureus* |
| Blank Example | 8.00E+08 | 8.00E+08 |
| 2 | 1.50E+01 | 0.00E+00 |
| 3 | 0.00E+00 | 0.00E+00 |
| 4 | 0.00E+00 | 0.00E+00 |

TABLE 1a-continued

Organobismuth complexes and the corresponding ligands tested against *E. coli* and *S. aureus*.

| Bismuth Complex | Colony | |
|---|---|---|
| | *E. coli* | *S. aureus* |
| 5 | 0.00E+00 | 0.00E+00 |
| Blank Comparative Example | 6.40E+08 | 4.00E+08 |
| 6 | 8.00E+07 | 5.00E+08 |
| 8 | 4.20E+08 | 2.00E+08 |
| 9 | 3.20E+08 | 6.00E+08 |
| Ligand | | |
| bis(4-methoxyphenyl)phosphinic acid | 8.00E+07 | 6.00E+08 |
| bis(3-nitrophenyl)phosphinic acid | 8.00E+07 | 8.00E+08 |
| phenylphosphinic acid | 3.20E+08 | 8.00E+08 |
| diphenylphosphinic acid | 2.40E+08 | 8.00E+08 |
| dimethyl phosphinic acid | 1.70E+08 | 6.00E+08 |

TABLE 1b

Organobismuth complexes and the corresponding ligands tested against *E. coli* and *S. aureus*.

| Bismuth Complex | Colony | |
|---|---|---|
| | *E. coli* | *S. aureus* |
| Blank Example | 4.00E+11 | 5.00E+11 |
| 1 Comparative Example | 0.00E+0 | 0.00E+0 |
| 7 | 9.00E+08 | 1.50E+12 |
| 10 | 2.00E+11 | 8.00E+10 |

Example organobismuth (III) phosphinate complexes of the invention showed a $10^8$ or $10^{11}$ reduction in colony growth compared to the control. Interestingly, the comparative example triphosphinate bismuth complexes tested at the same concentration showed worse antimicrobial activity.

Table 2 shows the results against *E. coli* and *S. aureus* presented as percentage reduction in bacterial growth (normalised against the Blank sample). The experiments were also repeated in a lower concentration (0.5 mg/mL) in accordance with the procedure above, which is also shown in Table 2.

TABLE 2

Organobismuth complexes and the corresponding ligands tested against *E. Coli* and *S. aureus*. Data has been normalised against the Blank sample. The method used to gather this data is the same as that used for gathering the data of Tables 1a and 1b, though additional data has been obtained at a lower concentration (0.5 mg/mL) of bismuth complex.

| | *E. coli* | | *S. aureus* | |
|---|---|---|---|---|
| | Reduction in bacterial growth (%) | | | |
| | 2 mg/mL | 0.5 mg/mL | 2 mg/mL | 0.5 mg/mL |
| Bismuth Complex | | | | |
| 1 | 100.00 | 100.00 | 100.00 | 100.00 |
| 2 | 100.00 | 100.00 | 100.00 | 40.00 |
| 3 | 100.00 | 97.00 | 100.00 | 90.00 |
| 4 | 100.00 | 100.00 | 100.00 | 100.00 |
| 5 | 100.00 | 100.00 | 100.00 | 100.00 |
| 6 | 90.00 | — | 37.50 | — |
| 7 | 99.78 | — | — | — |
| 8 | 34.38 | — | 50.00 | — |
| 9 | 60.00 | — | 25.00 | — |
| 10 | 50.00 | — | 84.00 | — |
| Ligand | | | | |
| bis(4-methoxyphenyl) phosphinic acid | 90.00 | — | 25.00 | — |
| bis(3-nitrophenyl) phosphinic acid | 90.00 | — | 0 | — |
| phenylphosphinic acid | 60.00 | — | 0 | — |
| diphenylphosphinic acid | 70.00 | — | 0 | — |
| dimethyl phosphinic acid | 78.75 | — | 25.00 | — |

(A dash ('—') indicates data not collected).

The data shown in Table 2 confirms that the example complexes demonstrate complete reduction in bacterial growth against both the gram negative *E. coli* strain of bacteria and the gram positive *S. aureus* strain of bacteria.

Antibacterial Testing Against MRSA (Methicillin Resistant *Staphylococcus aureus* and VRE (Vancomycin Resistant *Enterococcus*)

Testing of example organobismuth (III) phosphinate complexes of the invention also revealed antibacterial activity against the multi resistant bacterial strains MRSA (methicillin resistant *Staphylococcus aureus*) and VRE (vancomycin resistance *Enterococcus*). Using antibacterial test 1 as described above, but with MRSA and VRE in place of *E. coli* and *S. aureus*, a zoning effect was observed. The organobismuth (III) phosphinate complexes 1-5 appeared to be inhibiting growth.

To further investigate the antimicrobial properties of the organobismuth (III) phosphinate complexes against methicillin resistant *Staphylococcus aureus* (MRSA) and vancomycin-resistant *Enterococcus* (VRE), test method 2 was employed.

Figure 2:
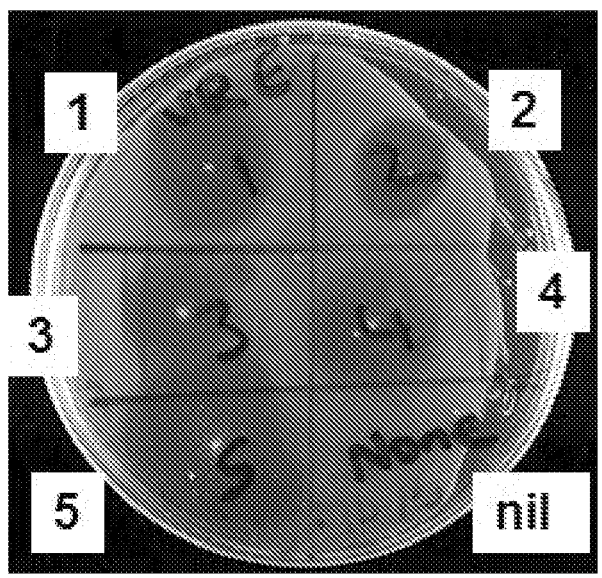
FIG. 2 shows a photograph of a zone of inhibition test showing inhibition of growth of VRE on BHI agar by example complexes 1-5.
Figure 3:
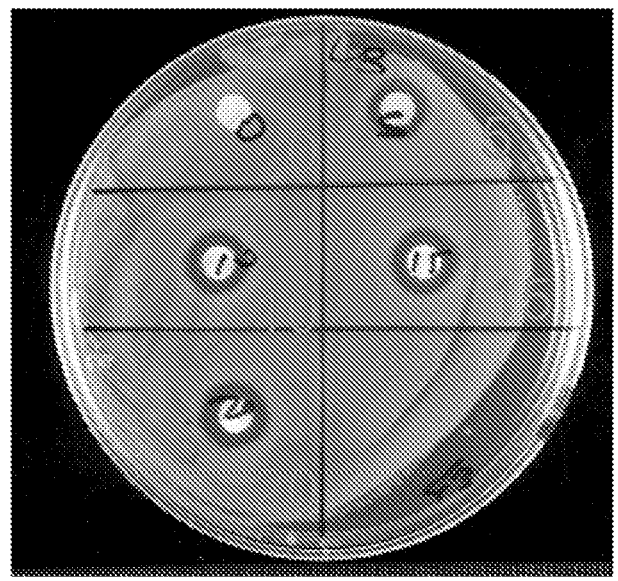
FIG. 3 shows a photograph of a zone of inhibition test showing inhibition of growth of E. Coli on BHI agar by cellulose-based paper containing 0%, 5%, 10%, 15% and 20% of example complex 1.
Figure 4:
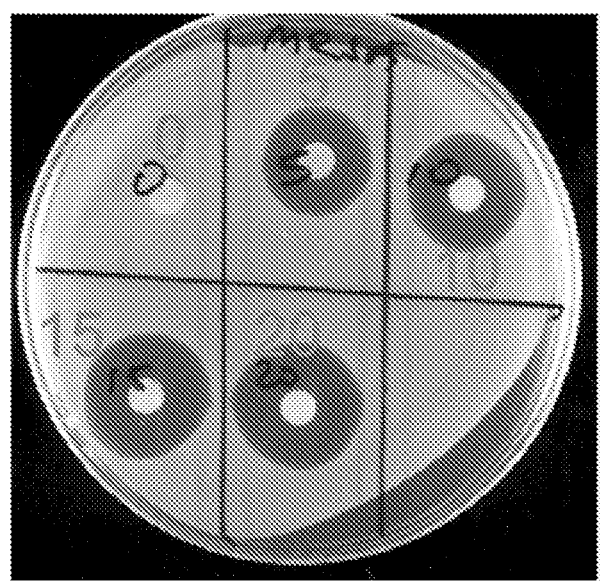
FIG. 4 shows a photograph of a zone of inhibition test showing inhibition of growth of MRSA on BHI agar by cellulose-based paper containing 0%, 5%, 10%, 15% and 20% of example complex 1.
Figure 5:
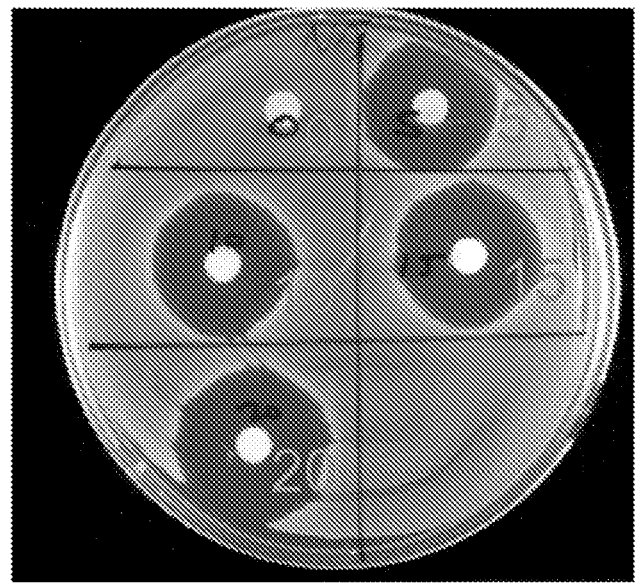
FIG. 5 shows a photograph of a zone of inhibition test showing inhibition of growth of S. Aureus on BHI agar by cellulose-based paper containing 0%, 5%, 10%, 15% and 20% of example complex 1.
Figure 6:
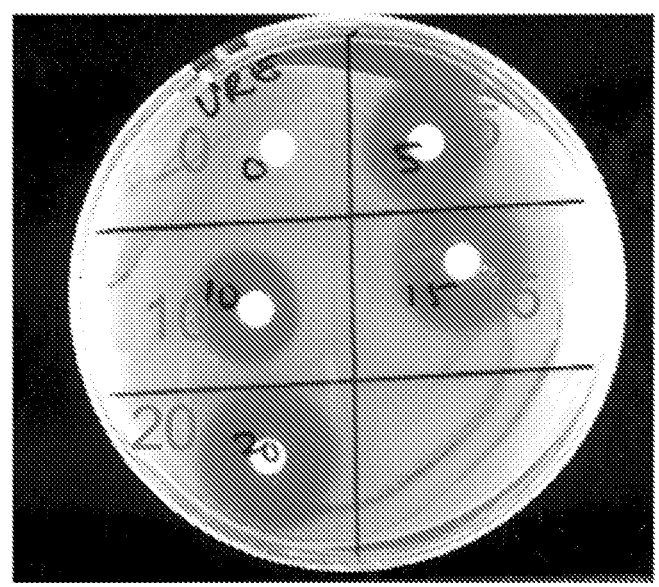
FIG. 6 shows a photograph of a zone of inhibition test showing inhibition of growth of VRE on BHI agar by cellulose-based paper containing 0%, 5%, 10%, 15% and 20% of example complex 1.

Test 2:

Zone of inhibition test to determine the susceptibility of the bacteria (MRSA and VRE) to the organobismuth (III) phosphinate compounds. Bacteria were grown overnight and then spread onto BHI (brain heart infusion) agar plates. Pipette tips were used to transfer a small quantity (<1 mg) of the organobismuth (III) phosphinate complex to the BHI agar plates. The pipette tip containing the complex was gently stabbed into the bacterial agar. The plates were allowed to grow overnight and the 'zone of inhibition' was visualised and images taken, using a BIO Rad Gel Doc XR+ Imaging System. Qualitative data revealed that MRSA and VRE are both susceptible to example complexes 1-5 (as defined above), as shown respectively by FIGS. 1 and 2. No bacteria growth was observed in a zone around the each bismuth complex. The organobismuth (III) phosphinate complexes exhibit antibacterial properties against MRSA and VRE.

When the same testing was carried out using the phosphinic acid ligands, bacterial growth was not inhibited.

Use of Organobismuth (III) Phosphinate Complexes Incorporated in a Matrix Demonstrating Antibacterial Activity To demonstrate the antibacterial properties of the organobismuth (III) phosphinate complexes when incorporated within compositions, test method 3 was employed.

Test 3:

The organobismuth (III) phosphinate complex (10 mg or 1 mg) was spread at the bottom of a petri dish. 20 mL of agar was poured on top, before allowing to dry and being stored in a cool dry place. MRSA and VRE were grown in 40 mL BHI with shaking at 37° C. to an OD (optical density) of 0.6 (2-3 hr). The bacteria were then grown for a further 2 hours at 37° C. The bacteria were then plated (at no dilution, $10^3$-fold dilution, and $10^4$-fold dilution on agar plates containing organobismuth (III) phosphinate and control plates containing no organobismuth (III) phosphinate. The plates were incubated overnight at 37° C. The colonies were counted and multiplied by the dilution factor to determine the colony-forming unit (cfu)/ml of the original culture.

When bacterial colonies were plated directly onto agar (20 mL), which had been treated with organobismuth (III) phosphinate complex 3 (1 mg), no bacterial growth was observed. The organobismuth (III) phosphinate complexes exhibited microbicidal properties. The organobismuth (III) phosphinate-containing agar was acting like an antimicrobial material by preventing the growth of bacteria.

The starting complex, triphenylbismuth was used as a comparator. When that was used as an additive to the agar (at the same concentration), the bacterial colonies grew to a comparable number as the blank (i.e.: no additive).

Use of Organobismuth (III) Phosphinate Complexes as a Coating Demonstrating Antibacterial Activity Similar experiments to those described above under test 3 were carried out in which, instead of being incorporated into an agar composition, the organobismuth (III) phosphinate complexes were added to the top of the agar. In those experiments, bacterial growth was also inhibited. This further demonstrates the ability of the complexes to act as a coating for surfaces having antibacterial properties.

Toxicity Testing

Toxicity testing was performed on the example complexes 1-5 as well as the corresponding ligands against cos 7 eukaryotic cells. Cytotoxicity was assessed using the MTT-based toxicology assay (Sigma-Aldrich; TOX1 assay kit) according to the manufacturer's instructions. Compounds were added to cultured cos 7 (monkey kidney-derived) cells at 1 mg/mL and 0.5 mg/mL for two hours. The MTT reagent was then added and cells were incubated at 37° C. for a further two hours. Following incubation, MTT solubilisation solution was added and mixed. Absorbance results were measured on a Tecan plate reader at 690 nm (background reading) and again at 570 nm. Results were calculated after subtracting the background reading (690 nm) from the values obtained at 570 nm. Cell viability was expressed as a normalised percentage against the blank (medium-only) negative controls. All assays were performed in duplicate.

Preliminary results indicated that organobismuth (III) phosphinate complexes 1, 4 and 5 were relatively non-toxic at concentrations of 1 mg/mL. Cos 7 cells which had been incubated with those complexes had a normalised cell viability of at least <60% that of blank or control Cos 7 cells, to which no complex was added. The organobismuth (III) phosphinate complexes showed no cytotoxicity when incubated at a concentration of 0.5 mg/mL.

Stability Properties of the Organobismuth (III) Phosphinate Complexes

The organobismuth (III) phosphinate complexes 1-5 were tested for their thermal and hydrolytic stability. Decomposition points for the complexes were found to range from 180° C. to >300° C. The complexes were also found to demonstrate good hydrolytic stability. Example organobismuth (III) phosphinate complexes according to the invention were also found to be insoluble both in organic and aqueous media.

Incorporation of Organobismuth (III) Phosphinate Complexes into Cellulose

Example complex 1 was incorporated into cellulose to produce a bismuth-containing paper with loadings of example complex 1 from 5-20%.

Preparation of Bismuth Complex Suspension

A bismuth suspension was prepared by dispersing bismuth complex 1 in a 20% isopropanol aqueous solution at 0.2 wt % for 24 hours. The solution was dispersed at room temperature using a magnetic stirrer.

Preparation of Micro-Fibrillated Cellulose (MFC) Suspension

Using a 3 L disintegrator, MFC was disintegrated at 0.2 wt % using deionised water.

Preparation of Cationic Polyelectrolyte (CPAM)

CPAM (cationic polyacrylamide) was prepared by dissolving CPAM polymer in deionised water at 0.01 wt % for 8 hours, at room temperature using a magnetic stirrer.

Preparation of Cellulose-Bismuth Paper

Preparation of the cellulose-bismuth paper used 0.2 g of MFC from the prepared 0.2 wt % suspension, an appropriate amount of bismuth complex from the prepared 0.2 wt % solution, and 10 mg/g of CPAM from the CPAM solution (10 mg/g of MFC).

To obtain 5% bismuth loading of example complex 1, 0.06 g of bismuth from a 0.2 wt % suspension was used. Similarly, 0.12 g was used for 10% loading, 0.18 g was used for 15% loading, and 0.4 g was used for 20% loading of bismuth complex 1.

Preparation of cellulose-bismuth suspension occurred in a two-step process. Bismuth complex and CPAM solutions were carefully mixed, prior to the CPAM-bismuth suspension and MFC suspension being mixed. The final suspension was then poured through a British hand sheet maker and the suspension was allowed to filter under gravity. Once a thin film had formed on the copper mesh, the film was removed using blotting papers and then dried using a drier at 105° C.

Preparation of Pure Cellulose Paper 1.2 g of 0.2 wt % MFC suspension was poured through a British hand sheet maker and the film formed on the mesh was taken out and dried using a drier at 105° C.

Assessment of Antibacterial Activity

The paper sheets were used in a Kirby-Bauer like test. The bismuth-containing paper was cut into small discs, which were then plated onto agar that had been spread with one of E. coli, S. aureus, MRSA or VRE bacterium. The agar plates with the discs were incubated overnight and observed the following morning. The experiments were conducted in triplicate (i.e. three agar plates per bacterial strain).

The results are shown in FIGS. 3 to 6. The figures demonstrate that, with each of the different bacteria, there is a clear zone of inhibition observed around the paper discs following incubation. This indicates that each of the bacteria tested are susceptible to this bismuth-containing paper, and that the bismuth-containing paper is acting as an antibacterial material.

SUMMARY

Bacteria continue to build resistance to the available antibiotics, and there is a need for new types of antimicrobial agents. The above results show the antimicrobial activity of the organobismuth (III) phosphinate complexes of the present disclosure. The present complexes provide a novel way to combat microbial spread, especially in hospitals. Organobismuth (III) phosphinate complexes of the present disclosure have excellent properties for application as additives to polymers (or other materials) to form antimicrobial surfaces or coatings. Example organobismuth (III) phosphinate complexes of the present disclosure have also been found to have high thermal and hydrolytic stability. Example organobismuth (III) phosphinate complexes have further been found to be insoluble in solvents. Thus, complex leaching or decomposition is unlikely.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. An organobismuth (III) phosphinate complex having a structure comprising formula (a):

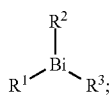

(a)

wherein
$R^1$ is a phosphinate group;
$R^2$ is an aromatic carbocyclyl or aromatic heterocyclyl group; and
$R^3$ is a phosphinate group, an aromatic carbocyclyl or aromatic heterocyclyl group, or a ligand;
and wherein the complex is not

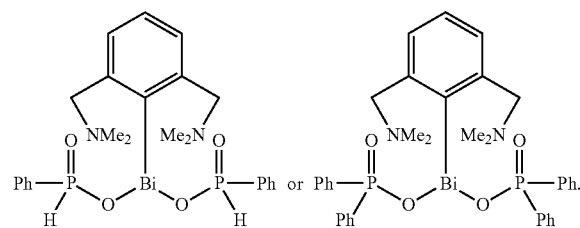

2. The complex of claim 1, wherein $R^3$ is a phosphinate group, or an aromatic carbocyclyl or aromatic heterocyclyl group.

3. The complex of claim 2, wherein $R^3$ is a phosphinate group.

4. The complex of claim 1, wherein the phosphinate group has the formula (b)

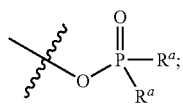

(b)

and each $R^a$ is independently selected from the group consisting of hydrogen, optionally substituted $C_{1-10}$alkyl, optionally substituted $C_{2-10}$alkenyl, optionally substituted $C_{2-10}$alkynyl, optionally substituted $C_{3-10}$ carbocyclyl and optionally substituted $C_{3-10}$ heterocyclyl.

5. The complex of claim 4, wherein the complex has the formula (c)

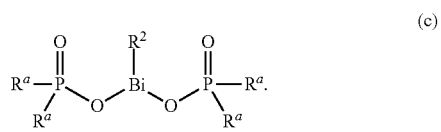

(c)

6. The complex of claim 5, wherein each $R^a$ is hydrogen.

7. The complex of claim 5, wherein each $R^a$ is unsubstituted $C_{1-6}$ alkyl.

8. The complex of claim 5, wherein each $R^a$ is $C_{6-10}$ aromatic carbocyclyl or $C_{6-10}$ aromatic heterocyclyl, said aromatic carbocyclyl or aromatic heterocyclyl being unsubstituted or substituted with up to 3 substituents selected from the group consisting of halogen, —CN, —NO$_2$, —C$_{1-6}$alkyl, —C$_{2-6}$alkenyl, —C$_{2-6}$alkynyl and —OC$_{1-6}$alkyl.

9. The complex of claim 5, wherein $R^a$ is selected from the group consisting of hydrogen, $C_{1-6}$alkyl, $C_{6-10}$ aromatic carbocyclyl or $C_{5-10}$ aromatic heterocyclyl, said aromatic carbocyclyl or aromatic heterocyclyl being unsubstituted or substituted with up to 3 substituents selected from the group consisting of halogen, —CN, —NO$_2$, —C$_{1-6}$alkyl, —C$_{2-6}$alkenyl, —C$_{2-6}$alkynyl and —OC$_{1-6}$alkyl; and $R^2$ is $C_{6-10}$ aromatic carbocyclyl or $C_{5-10}$ aromatic heterocyclyl, said aromatic carbocyclyl or aromatic heterocyclyl being unsubstituted or substituted with up to 3 substituents each independently selected from the group consisting of halogen, —CN, —NO$_2$, C$_{1-6}$alkyl, —C$_{2-6}$alkenyl, —C$_{2-6}$alkynyl and —OC$_{1-6}$alkyl.

10. The complex of claim 1, wherein $R^2$ is $C_{6-10}$ aromatic carbocyclyl or $C_{5-10}$ aromatic heterocyclyl, said aromatic carbocyclyl or aromatic heterocyclyl being unsubstituted or substituted with up to 3 substituents each independently selected from the group consisting of halogen, —CN, —NO$_2$, C$_{1-6}$alkyl, —C$_{2-6}$alkenyl, —C$_{2-6}$alkynyl and OC$_{1-6}$alkyl.

11. The complex of claim 10, wherein $R^2$ is phenyl which is unsubstituted or substituted with up to 3 substituents each independently selected from the group consisting of halogen, —CN, —NO$_2$, C$_{1-6}$alkyl, —C$_{2-6}$alkenyl, —C$_{2-6}$alkynyl and OC$_{1-6}$alkyl.

12. The complex of claim 1, wherein the complex is selected from the group consisting of:

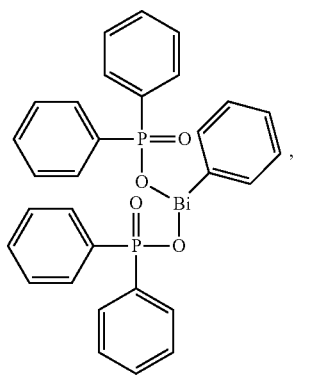

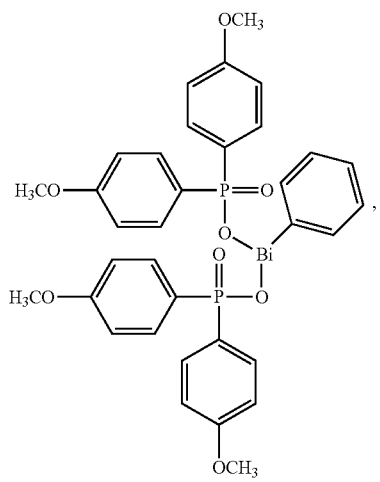

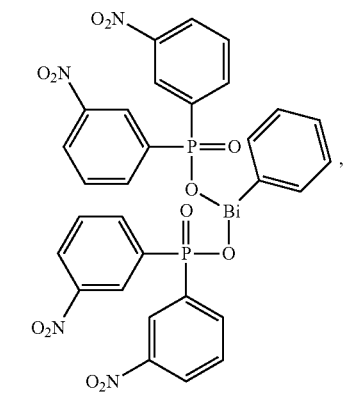

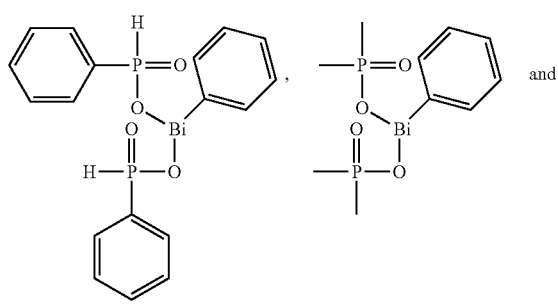

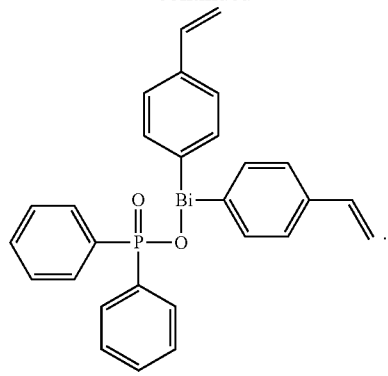

13. The complex of claim 1, wherein the complex is:

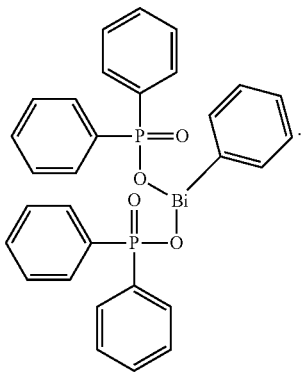

14. A product, device, material, or composition comprising a complex of claim 1.

15. The product, device, material, or composition of claim 14, wherein the product, device, material or composition comprises an antibacterial surface coating comprising the complex.

16. The composition of claim 14, wherein the composition is a polymerisable and/or curable composition.

17. The product, device, material, or composition of claim 15, wherein the product, device, material, or composition is a wound dressing, a suture, a surgical implement, or a medical implant.

18. The product, device, composition, or material of claim 14, wherein the product, device, material, or composition is a medical adhesive, a bone cement, a dental adhesive or a dental filler composition.

19. The product, device, material, or composition of claim 14, wherein the product, device, material, or composition is for use in building construction, renovation, and/or maintenance and wherein the product, device, material, or composition is a coating, sealant, cement, concrete, grout, mortar, or stucco composition.

20. The product, device, material, or composition of claim 14, wherein the product, device, material, or composition comprises antibacterial packaging comprising the complex.

21. The product, device, material, or composition of claim 14, wherein the product, device, material, or composition is a cellulosic material.

* * * * *